United States Patent [19]
Adams, Jr. et al.

[11] Patent Number: 5,223,523
[45] Date of Patent: Jun. 29, 1993

[54] FUNGICIDAL OXAZOLIDINONES

[75] Inventors: John B. Adams, Jr., Hockessin, Del.; Detlef Geffken, Hamburg, Fed. Rep. of Germany; Dennis R. Rayner, Centerville, Del.

[73] Assignee: E.I. Du Pont de Nemours and Company, Wilmington, Del.

[21] Appl. No.: 778,079

[22] PCT Filed: Apr. 10, 1990

[86] PCT No.: PCT/US90/02076

§ 371 Date: Dec. 12, 1991

§ 102(e) Date: Dec. 12, 1991

Related U.S. Application Data

[63] Continuation-in-part of Ser. No. 341,741, Apr. 21, 1989, Pat. No. 4,957,933, and a continuation-in-part of Ser. No. 341,742, Apr. 21, 1989, abandoned.

[51] Int. Cl.$^5$ .................... C07D 263/00; C07D 413/00
[52] U.S. Cl. .................................... 514/376; 514/212; 514/252; 514/256; 514/326; 514/340; 514/375; 540/524; 548/216; 548/226; 546/16; 546/209
[58] Field of Search ............... 514/376; 548/216, 226, 548/228

[56] References Cited

U.S. PATENT DOCUMENTS

| | | | |
|---|---|---|---|
| 2,037,717 | 4/1936 | Graves | 558/245 |
| 2,559,011 | 3/1951 | Davies | 548/226 |
| 2,928,840 | 3/1960 | Shapiro et al. | 548/226 |
| 3,054,794 | 9/1962 | Shapiro et al. | 548/226 |
| 3,773,782 | 11/1973 | Zelinski | 548/226 |
| 4,342,773 | 8/1982 | DiToro et al. | 514/376 |
| 4,436,744 | 3/1984 | Harr | 514/376 |
| 4,477,461 | 10/1984 | Gallaschelli et al. | 514/376 |
| 4,957,933 | 9/1990 | Geffken et al. | 514/376 |

FOREIGN PATENT DOCUMENTS

| | | |
|---|---|---|
| 241559 | 10/1987 | European Pat. Off. |
| 2324591 | 12/1974 | Fed. Rep. of Germany |
| 2805957 | 8/1978 | Fed. Rep. of Germany |
| 0216882 | 12/1984 | Japan .................. 548/226 |

OTHER PUBLICATIONS

Geffken, Synthesis No. 1, 1981, pp. 38–40.
Geffken, Chem. Abstr. vol. 100, Entry 6469q (1984).
Geffken, Chem. Abstr. vol. 97, Entry 182374b (1982).
Geffken, Chem. Abstr. vol. 92 Entry 110894b (1980).
Geffken, Chem. Abstr. vol. 94 Entry 103215u (1981).
Geffken, Chem. Abstr. vol. 106 entry 18462u (1987).
Davidson, Chem. Abstr. vol. 98 entry 89276P (1983).

*Primary Examiner*—Donald G. Daus

[57] ABSTRACT

Compounds for an methods of controlling plant diseases using thiooxazolidinones, oxazolidindiones and agriculturally suitable compositions containing them are disclosed.

14 Claims, No Drawings

FUNGICIDAL OXAZOLIDINONES

CROSS-REFERENCE TO RELATED APPLICATION

This application is a continuation-in-part of our co-pending application U.S. Ser. No. 07/341,741, filed on Apr. 21, 1989, now U.S. Pat. No. 4,957,933 and of co-pending application U.S. Ser. No. 341,742 filed Apr. 21, 1989, now abandoned. This application was originally filed as international application number PCT/US90/02076 on Apr. 10, 1990, from which priority is claimed.

BACKGROUND OF THE INVENTION

This invention pertains to a novel method-of-use of compounds of Structure I as fungicides for protecting plants from disease.

Processes for the preparation of the compounds described in this invention are disclosed in the following references:

Geffken, D.; *Z. Naturforsch*, 1983, 38b, 1008
Geffken, D.; Zinner, G.; *Chem. Ber.*, 1973, 106, 2246
Geffken, D.; *Arch. Pharm.*, 1982, 315, 802;
Geffken, D.; *Z. Naturforsch*, 1987, 42b, 1202

No particular utility for the compounds is described in the above references.

A new process for the preparation of these compounds is also disclosed in this application.

Compounds related to I are broadly disclosed as medicines, agrochemicals and microbicides in Japanese Patent 61/200978-A, and as general biocides in EP 249328-A. However, these applications do not encompass compounds of the instant invention, nor do they suggest the use of the compounds of this invention as fungicides particularly effective for the protection of crops against disease.

SUMMARY OF THE INVENTION

This invention comprises a method of controlling fungus disease in plants that comprises treating the locus to be protected with an effective amount of a compound of Formula I,

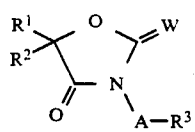

wherein:
A is O or $NR^4$;
W is O or S;
$R^1$ is H; $C_1$ to $C_6$ alkyl; $C_1$ to $C_6$ haloalkyl; $C_3$ to $C_6$ cycloalkyl; $C_2$ to $C_6$ alkenyl; $C_2$ to $C_6$ alkynyl; $C_2$ to $C_6$ alkoxyalkyl; $C_1$ to $C_3$ alkyl substituted with $C_3$ to $C_6$ cycloalkyl, phenyl or benzyl, wherein said phenyl or benzyl ring is substituted on the ring with $R^6$, and the benzylic carbon is substituted with $R^7$;
$R^2$ is phenyl substituted with $R^5$ and $R^6$; naphthyl substituted with 1 to 2 groups selected from $R^6$; thienyl substituted with $R^5$ and $R^6$; furyl substituted with $R^6$; pyridyl substituted with one of the following:
  $R^6$, phenoxy substituted with $R^6$, or phenylthio substituted with $R^6$;
  $C_1$ to $C_2$ alkyl substituted with phenoxy or phenylthio, said phenoxy or phenylthio being substituted on the ring with $R^6$;
  $C_1$ to $C_6$ alkyl; or
  $C_5$ to $C_7$ cycloalkyl; and
$R^1$ and $R^2$ can be taken together, along with the carbon to which they are attached, to form a carbocyclic or heterocyclic ring (containing O, N-$R^7$, or S) of 5 to 7 ring atoms in which the heterocyclic ring can be fused with an $R^5$-substituted benzene ring or an $R^6$-substituted thiophene ring, the heteroatom not being attached to the spiro center; and the carbocyclic ring can be fused with 1 or 2 $R^5$-substituted benzene rings or with an $R^6$-substituted thiophene ring;
$R^3$ is phenyl substituted with $R^{10}$; benzyl substituted on the benzylic carbon with a group selected from $R^7$ and substituted on the phenyl ring with $R^{10}$; naphthyl substituted with $R^{10}$; additionally, $R^3$ can be thienyl substituted with $R^{10}$, furyl substituted with $R^{10}$, pyridyl substituted with $R^{10}$, pyrimidyl substituted with $R^{10}$, or pyridazyl substituted with $R^{10}$; or $R^3$ can be $C_2$ to $C_{10}$ alkyl or $C_5$ to $C_7$ cycloalkyl;
$R^4$ is hydrogen; formyl; $C_2$ to $C_4$ alkylcarbonyl; $C_2$ to $C_4$ haloalkylcarbonyl; $C_2$ to $C_4$ alkoxyalkylcarbonyl; $C_2$ to $C_4$ alkoxycarbonyl; $C_2$ to $C_5$ alkylaminocarbonyl; $C_1$ to $C_4$ alkylsulfonyl; $C_1$ to $C_4$ alkyl; $C_4$ to $C_6$ cycloalkyl; phenylaminocarbonyl where said phenyl is substituted with $R^{10}$; and $R^4$ can be $C_3$ to $C_4$ alkenyl or $C_3$ to $C_4$ alkynyl; or
$R^3$ and $R^4$ can be taken together, along with the nitrogen atom to which they are attached, to form a pyrrolidino, piperidino or pyrrolo ring substituted with $R^{10}$, which rings can be fused to an $R^{10}$-substituted benzene ring;
$R^5$ is hydrogen; halogen; $C_1$ to $C_{12}$ alkyl; $C_1$ to $C_{12}$ haloalkyl; $C_1$ to $C_{12}$ alkoxy; $C_3$ to $C_{12}$ alkenyl; $C_3$ to $C_{12}$ haloalkenyl; $C_3$ to $C_{12}$ alkenyloxy; $C_3$ to $C_{12}$ alkynyl; $C_3$ to $C_{12}$ haloalkynyl; $C_3$ to $C_{12}$ alkylthio; $C_1$ to $C_{12}$ haloalkylthio; $C_1$ to $C_{12}$ haloalkoxy; $C_1$ to $C_{12}$ alkylsulfonyl; $C_1$ to $C_{12}$ haloalkylsulfonyl; nitro; phenyl substituted with $R^6$; phenoxy substituted with $R^6$; phenylthio substituted with $R^6$; cyano; $C_3$ to $C_{12}$ alkynyloxy; $C_2$ to $C_{12}$ alkoxyalkyl; $C_2$ to $C_{12}$ alkoxyalkoxy; phenoxymethyl substituted on the phenyl ring with $R^6$; benzyloxy substituted on the phenyl ring with $R^6$; phenethyloxy substituted on the phenyl ring with $R^6$; phenethyl substituted on the phenyl ring with $R^6$; benzyl substituted on the phenyl ring with $R^6$; $C_2$ to $C_{12}$ carboalkoxy; $C_5$ to $C_6$ cycloalkyl; $NMe_2$; or $NR^8R^9$;
$R^6$ is hydrogen; 1 to 2 halogen; $C_1$ to $C_4$ alkyl; trifluoromethyl; $C_1$ to $C_4$ alkoxy; methylthio; nitro; phenoxy; $C_2$ to $C_6$ cycloalkyloxy; or $C_5$ to $C_6$ cycloalkyl;
$R^7$ is hydrogen; or $C_1$ to $C_4$ alkyl;
$R^8$ is H; or $C_1$ to $C_4$ alkyl;
$R^9$ is H; phenyl substituted with H; 1-2 halogen; $CF_3$; $C_1$ to $C_2$ alkyl; or $C_1$ to $C_2$ alkoxy; and
$R^{10}$ is 0-2 groups selected from H; $CF_3$; $CF_3O$; $NO_2$; $CO_2Me$; halogen; $C_1$ to $C_5$ alkyl; $C_1$ to $C_5$ alkoxy; or CN; provided that when the phenyl ring is disubstituted, one of the alkyl or alkoxy groups is no larger than $C_1$;

provided that, when A is oxygen, $R^3$ is phenyl substituted with $R^5$ and $R^6$, Preferred for greatest fungicidal activity and/or ease of synthesis are:

2. The method of Preferred 1 wherein
   A is NR$^4$;
   R$^1$ is C$_1$ to C$_4$ alkyl; C$_1$ to C$_3$ haloalkyl; vinyl; ethynyl; or methoxymethyl;
   R$^2$ is phenyl substituted with R$^5$ and R$^6$; C$_5$ to C$_7$ cycloalkyl; thienyl substituted with R$^6$; or pyridyl substituted with R$^6$;
   R$^3$ is phenyl substituted with R$^{10}$; and
   R$^4$ is H; C$_1$ to C$_3$ alkyl; or C$_1$ to C$_3$ alkylcarbonyl.

3. The method of Preferred 2 wherein
   R$^1$ is C$_1$ to C$_4$ alkyl or vinyl;
   R$^2$ is phenyl substituted with R$^5$ and R$^6$;
   R$^3$ is phenyl substituted with 1-2 halogen, methyl or methoxy;
   R$^4$ is hydrogen or methyl;
   R$^5$ is hydrogen; halogen; C$_1$ to C$_4$ alkyl; C$_1$ to C$_4$ haloalkyl; C$_1$ to C$_6$ alkoxy; benzyloxy; F$_3$CO; F$_2$HCO; C$_1$ to C$_6$ haloalkoxy; phenoxy substituted with R$^6$; provided that if R$^5$ is not H or F, then it is para to the point of attachment to the ring;
   R$^6$ is hydrogen, 1 to 2 F or Cl; methyl; or methoxy; and
   R$^7$ is hydrogen.

4. The method of Preferred 3 wherein
   R$^1$ is CH$_3$;
   R$^4$ is hydrogen or methyl;
   R$^5$ is H; F; Cl; CH$_3$; C$_1$ to C$_6$ alkoxy; or phenoxy substituted with halogen, CH$_3$, CH$_3$O or NO$_2$;
   R$^6$ is H or F; and
   R$^{10}$ is F; H or CH$_3$.

Specifically preferred for greatest fungicidal activity and/or ease of synthesis are methods utilizing:

5-methyl-5-(4-phenoxyphenyl)-3-(phenyl-   (1)
amino)-2-thioxo-4-oxazolidinone;
and the (S)-enantiomer thereof.

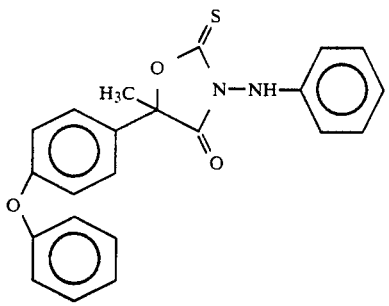

5-methyl-5-phenyl-3-(-N'-phenyl-N'-methyl-   (2)
amino)-2-thioxo-4-oxazolidinone; and
the (S)-enantiomer thereof.

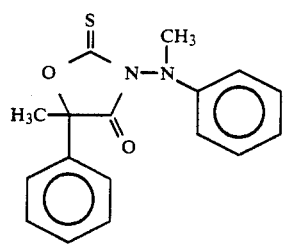

5-[4-(4-bromophenoxy)phenyl]-5-methyl-3-   (3)
(phenylamino)-2-thioxo-4-oxazolidinone;
and the (S)-enantiomer thereof.

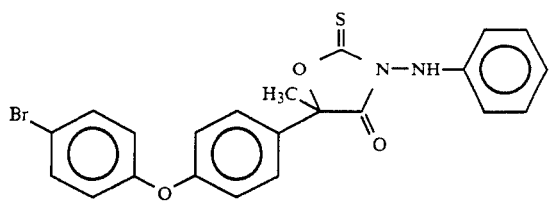

5-[4-(3-fluorophenoxy)phenyl]-5-methyl-3-   (4)
(phenylamino)-2-thioxo-4-oxazolidinone;
and the (S)-enantiomer thereof.

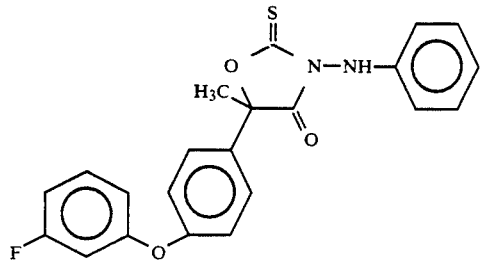

5-(2,4-difluorophenyl)-5-methyl-3-(phenyl-   (5)
amino)-2,4-oxazolidinedione; and the
(S)-enantiomer thereof.

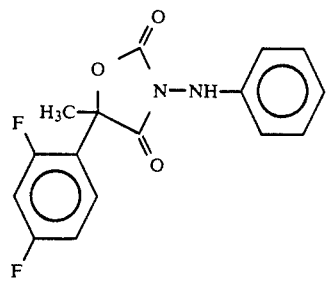

5-methyl-5-(4-phenoxyphenyl)-3-(phenyl-   (6)
amino)-2,4-oxazolidinedione; and the
(S)-enantiomer thereof.

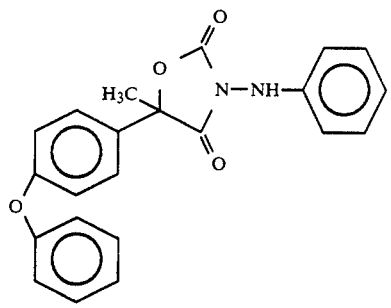

5-(2,5-difluorophenyl)-5-methyl-3-(phenyl-   (7)
amino)-2,4-oxazolidinedione; and the
(S)-enantiomer thereof.

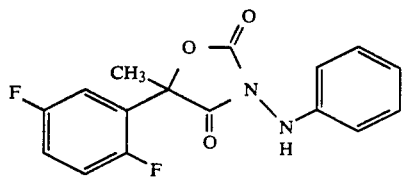

5-(2-fluorophenyl)-5-methyl-3-(phenyl-   (8)
amino)-2,4-oxazolidinedione; and the
(S)-enantiomer thereof.

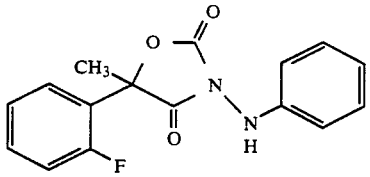

5-[4-(3-fluorophenoxy)phenyl]-5-methyl-3-(phenylamino)-2,4-oxazolidinedione; and the (S)-enantiomer thereof.    (9)

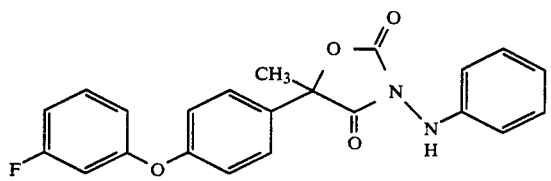

5.

This invention also comprises novel compounds of Formula IA,

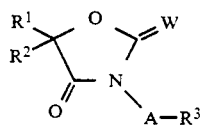

IA wherein:
A is O or $NR^4$;
W is O or S;
$R^1$ is H; $C_1$ to $C_6$ alkyl; $C_1$ to $C_6$ haloalkyl; $C_3$ to $C_6$ cycloalkyl; $C_2$ to $C_6$ alkenyl; $C_2$ to $C_6$ alkynyl; $C_2$ to $C_6$ alkoxyalkyl; $C_1$ to $C_3$ alkyl substituted with $C_3$ to $C_6$ cycloalkyl, phenyl or benzyl, wherein said phenyl or benzyl ring is substituted on the ring with $R^6$, and the benzylic carbon is substituted with $R^7$;
$R^2$ is phenyl substituted with $R^5$ and $R^6$; naphthyl substituted with 1 to 2 groups selected from $R^6$; thienyl substituted with $R^5$ and $R^6$; furyl substituted with $R^6$; pyridyl substituted with one of the following:
  $R^6$, phenoxy substituted with $R^6$, or phenylthio substituted with $R^6$;
  $C_1$ to $C_2$ alkyl substituted with phenoxy or phenylthio, said phenoxy or phenylthio being substituted on the ring with $R^6$;
  $C_1$ to $C_6$ alkyl; or
  $C_5$ to $C_7$ cycloalkyl; and
$R^1$ and $R^2$ can be taken together, along with the carbon to which they are attached, to form a carbocyclic or heterocyclic ring (containing O, N-$R^7$, or S) of 5 to 7 ring atoms in which the heterocyclic ring can be fused with an $R^5$-substituted benzene ring or an $R^6$-substituted thiophene ring, the heteroatom not being attached to the spiro center; and the carbocyclic ring can be fused with 1 or 2 $R^5$-substituted benzene rings or with an $R^6$-substituted thiophene ring;
$R^3$ is phenyl substituted with $R^{10}$; benzyl substituted on the benzylic carbon with a group selected from $R^7$ and substituted on the phenyl ring with $R^{10}$; naphthyl substituted with $R^{10}$; additionally, $R^3$ can be thienyl substituted with $R^{10}$, furyl substituted with $R^{10}$, pyridyl substituted with $R^{10}$, pyrimidyl substituted with $R^{10}$, or pyridazyl substituted with $R^{10}$; or $R^3$ can be $C_2$ to $C_{10}$ alkyl or $C_5$ to $C_7$ cycloalkyl;
$R^4$ is hydrogen; formyl; $C_2$ to $C_4$ alkylcarbonyl; $C_2$ to $C_4$ haloalkylcarbonyl; $C_2$ to $C_4$ alkoxyalkylcarbonyl; $C_2$ to $C_4$ alkoxycarbonyl; $C_2$ to $C_5$ alkylaminocarbonyl; $C_1$ to $C_4$ alkylsulfonyl; $C_1$ to $C_4$ alkyl; $C_4$ to $C_6$ cycloalkyl; phenylaminocarbonyl where said phenyl is substituted with $R^{10}$; and $R^4$ can be $C_3$ to $C_4$ alkenyl or $C_3$ to $C_4$ alkynyl; or
$R^3$ and $R^4$ can be taken together, along with the nitrogen atom to which they are attached, to form a pyrrolidino, piperidino or pyrrolo ring substituted with $R^{10}$, which rings can be fused to an $R^{10}$-substituted benzene ring;
$R^5$ is hydrogen; halogen; $C_1$ to $C_{12}$ alkyl; $C_1$ to $C_{12}$ haloalkyl; $C_1$ to $C_{12}$ alkoxy; $C_3$ to $C_{12}$ alkenyl; $C_3$ to $C_{12}$ haloalkenyl; $C_3$ to $C_{12}$ alkenyloxy; $C_3$ to $C_{12}$ alkynyl; $C_3$ to $C_{12}$ haloalkynyl; $C_3$ to $C_{12}$ alkylthio; $C_1$ to $C_{12}$ haloalkylthio; $C_1$ to $C_{12}$ haloalkoxy; $C_1$ to $C_{12}$ alkylsulfonyl; $C_1$ to $C_{12}$ haloalkylsulfonyl; nitro; phenyl substituted with $R^6$; phenoxy substituted with $R^6$; phenylthio substituted with $R^6$; cyano; $C_3$ to $C_{12}$ alkynyloxy; $C_2$ to $C_{12}$ alkoxyalkyl; $C_2$ to $C_{12}$ alkoxyalkoxy; phenoxymethyl substituted on the phenyl ring with $R^6$; benzyloxy substituted on the phenyl ring with $R^6$; phenethyloxy substituted on the phenyl ring with $R^6$; phenethyl substituted on the phenyl ring with $R^6$; benzyl substituted on the phenyl ring with $R^6$; $C_2$ to $C_{12}$ carboalkoxy; $C_5$ to $C_6$ cycloalkyl; NMe$_2$; or $NR^8R^9$;
$R^6$ is hydrogen; 1 to 2 halogen; $C_1$ to $C_4$ alkyl; trifluoromethyl; $C_1$ to $C_4$ alkoxy; methylthio; nitro; phenoxy; $C_2$ to $C_6$ cycloalkyloxy; or $C_5$ to $C_6$ cycloalkyl;
$R^7$ is hydrogen; or $C_1$ to $C_4$ alkyl;
$R^8$ is H; or $C_1$ to $C_4$ alkyl;
$R^9$ is H; phenyl substituted with H; 1-2 halogen; CF$_3$; $C_1$ to $C_2$ alkyl; or $C_1$ to $C_2$ alkoxy; and
$R^{10}$ is 0-2 groups selected from H; CF$_3$; CF$_3$O; NO$_2$; CO$_2$Me; halogen; $C_1$ to $C_5$ alkyl; $C_1$ to $C_5$ alkoxy; or CN; provided that when the phenyl ring is disubstituted, one of the alkyl or alkoxy groups is no larger than $C_1$;
provided that
(1) when A is O, then $R^3$ is phenyl substituted with $R^5$ or $R^6$;
(2) when $R^2$ is unsubstituted phenyl, then $R^1$ is not hydrogen, methyl or benzyl;
(3) when $R^1$ is hydrogen, methyl or cyclohexyl, then $R^2$ is not methyl, isopropyl or cyclohexyl; and
(4) $R^1$ and $R^2$ do not join to form —(CH$_2$)$_5$—.

Preferred for greatest fungicidal activity and/or ease of synthesis are:
6. A compound of Formula IA wherein
  A is $NR^4$;
  $R^1$ is $C_1$ to $C_4$ alkyl; $C_1$ to $C_3$ haloalkyl; vinyl; ethynyl; or methoxymethyl;
  $R^2$ is phenyl substituted with $R^5$ and $R^6$; $C_5$ to $C_7$ cycloalkyl; thienyl substituted with $R^6$; or pyridyl substituted with $R^6$;
  $R^3$ is phenyl substituted with $R^{10}$; and
  $R^4$ is H; $C_1$ to $C_3$ alkyl; or $C_1$ to $C_3$ alkylcarbonyl.
  provided that when $R^2$ is unsubstituted phenyl, $R^1$ is not methyl.

7. A compound of Formula IA wherein $R^1$ is $C_1$ to $C_4$ alkyl or vinyl;

$R^2$ is phenyl substituted with $R^5$ and $R^6$;

$R^3$ is phenyl substituted with 1–2 halogen, methyl or methoxy;

$R^4$ is hydrogen or methyl;

$R^5$ is hydrogen; halogen; $C_1$ to $C_4$ alkyl; $C_1$ to $C_4$ haloalkyl; $C_1$ to $C_6$ alkoxy; benzyloxy; $F_3CO$; $F_2HCO$; $C_1$ to $C_6$ haloalkoxy; phenoxy substituted with $R^6$; provided that if $R^5$ is not H or F, then it is para to the point of attachment to the ring;

$R^6$ is hydrogen, 1 to 2 F or Cl; methyl; or methoxy; and $R^7$ is hydrogen;

provided that when $R^2$ is unsubstituted phenyl, $R^1$ is not methyl.

8. A compound of Formula IA wherein $R^1$ is $CH_3$;

$R^4$ is hydrogen or methyl;

$R^5$ is H; F; Cl; $CH_3$; $C_1$ to $C_6$ alkoxy; or phenoxy substituted with halogen, $CH_3$, $CH_3O$ or $NO_2$;

$R^6$ is H or F; and $R^{10}$ is F; H or $CH_3$;

provided that $R^2$ is not unsubstituted phenyl.

Specifically preferred for greatest fungicidal activity and/or ease of synthesis are are the following compounds:

5-methyl-5-(4-phenoxyphenyl)-3-(phenyl-amino)-2-thioxo-4-oxazolidinone; and the (S)-enantiomer thereof. (1)

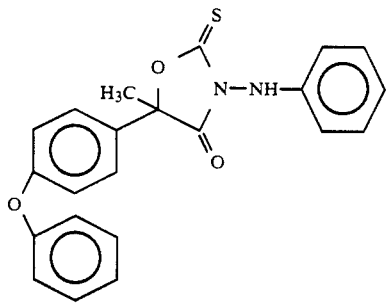

5-methyl-5-phenyl-3-(-N'-phenyl-N'-methyl-amino)-2-thioxo-4-oxazolidinone; and the (S)-enantiomer thereof. (2)

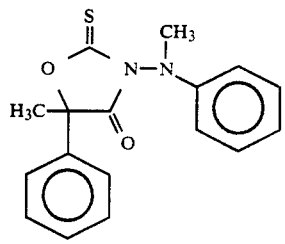

5-(4-(-bromophenoxy)phenyl)-5-methyl-3-(phenylamino)-2-thioxo-4-oxazolidinone; and the (S)-enantiomer thereof. (3)

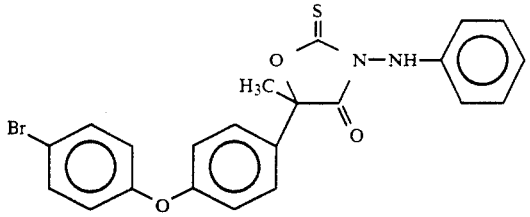

5-[4-(3-fluorophenoxy)phenyl]-5-methyl-3-(phenylamino)-2-thioxo-4-oxazolidinone; and the (S)-enantiomer thereof. (4)

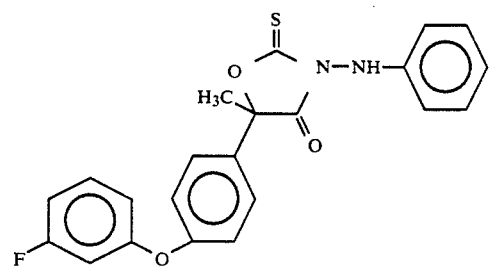

5-(2,4-difluorophenyl)-5-methyl-3-(phenyl-amino)-2,4-oxazolidinedione; and the (S)-enantiomer thereof. (5)

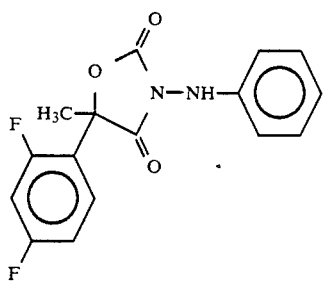

5-methyl-5-(4-phenoxyphenyl)-3-(phenyl-amino)-2,4-oxazolidinedione; and the (S)-enantiomer thereof. (6)

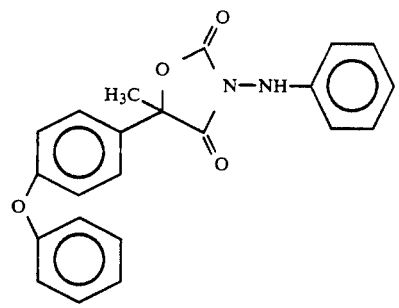

DETAILED DESCRIPTION OF THE INVENTION

Synthesis

The compounds of this invention may be prepared by the route outlined below to 5-methyl-5-phenyl-3-(phenylamino)-2-thioxo-4-oxazolidinone:

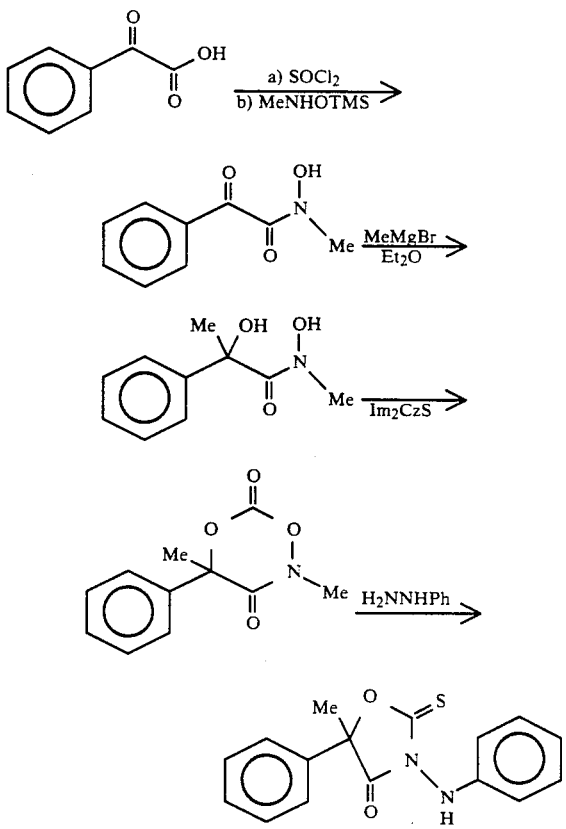

Details of these procedures and related variations are described in the following Equations.

One skilled in the art will recognize that when $R^1$ and $R^2$ are different, compounds of Formula I in Equation 1 possess a chiral center. This invention pertains to racemic mixtures and to pure enantiomers. Although one enantiomer may have superior fungicidal activity for a given compound of Formula I, the other enantiomer is not devoid of activity nor does it interfere with the activity of the more potent enantiomer.

As shown in Equation 1, compounds of Formula I can be prepared by treating heterocycles of type II with an appropriate amine III.

Equation 1

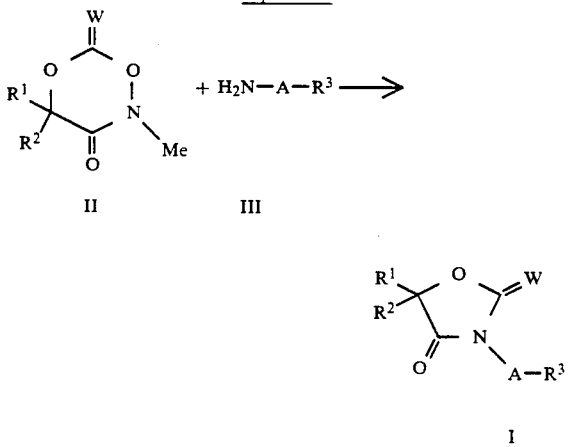

The reactions are conducted at 0° C. to 50° C. in an inert solvent such as methylene chloride, THF, or benzene. Detailed experimental procedures are disclosed in the references cited below.

Compounds described by Formula I wherein W is S can be prepared as illustrated in Equation 2.

Equation 2

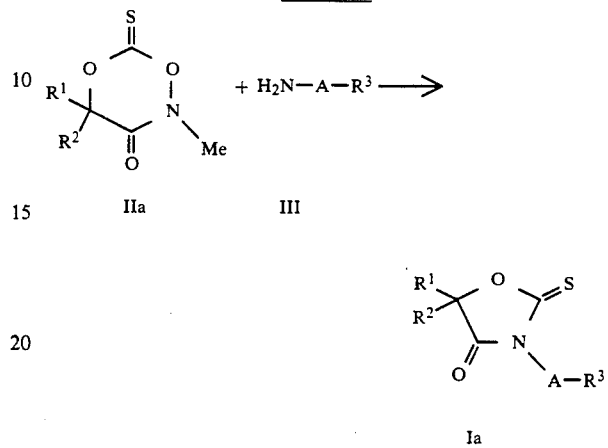

Treatment of thioxodioxazinones IIa with hydroxylamines (A=O) or hydrazines (A=NR$^4$) in an inert solvent such as methylene chloride, benzene, or THF at temperatures ranging from −10° C. to 35° C. gives the thioxooxazolidinones Ia. [Geffken, D.; Z. Naturforsch, 1983, 38b, 1008]

The thioxodioxazinones IIa are prepared according to the method outlined in Equation 3.

Equation 3

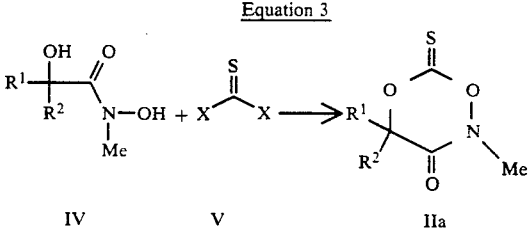

The hydroxamic acids IV are reacted with a thionoating agent V, such as thiophosgene (X=Cl) in the presence of a base or 1,1′-thiocarbonyldiimidazole (X=imidazole), to afford the thioxodioxazinones IIa. The reactions are performed at −20° C. to 25° C. in an inert solvent. [Geffken, D., Z. Naturforsch, 1983, 38b, 1008] The products are generally unstable at ambient temperature and therefore are reacted with the desired amine III immediately upon isolation.

Preparation of the hydroxylamines [Castellino, A. J.; Rapoport, H.; J. Org. Chem., 1984, 49, 1348] (III, A=O) and hydrazines [J. Timberlake; J. Stowell; The Chemistry of the Hydrazo, Azo, and Azoxy Groups (S. Patai, Ed.) John Wiley and Sons, Ltd, London (1975), p. 69; Demers, J. P.; Klaubert, D. J.; Tetrahedron Lett., 1987, 4933] (III, A=NR$^4$) can be accomplished by literature methods by one skilled in the art.

The synthesis of the requisite hydroxamic acids IV can be accomplished by several known methods. As shown in Equation 4, the condensation of an α-hydroxycarboxylic acid VI (Z=H) with N-methylhydroxylamine hydrochloride affords the desired hydroxamic acids IV. [Geffken, D.; Kampf, H.; J. Chem. Ztg., 1979, 103, 19] Triethylamine is commonly used as an added base and 1,3-dicyclohexylcarbodiimide (DCC) is used as the dehydrating agent.

Equation 4

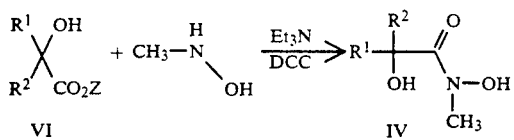

2-Hydroxycarboxylic acids can be purchased from commercial sources, or generally prepared from ketones or aldehydes by formation of cyanohydrins, then hydrolysis, as is known in the art. For example, Org. Syn. Coll. Vol. IV, 58 (1968) teaches the preparation of atrolactic acid from acetophenone. Esters can be prepared from the 2-hydroxycarboxylic acids by methods known in the art. Alternatively, aryl α-hydroxycarboxylic acid esters can also be prepared by treating pyruvate esters with nucleophilic organometallic reagents such as phenyl magnesium bromide or phenyl lithium as described in the literature (Salomon, R. G., Pardo, S. N., Ghosh, S., *J. Org. Chem.*, 1982, 47, 4692). The "Dictionary of Organic Compounds", Vol. 3, 4th ed. (1965), page 1791 (Oxford Univ. Press) lists atrolactic acid and esters.

Alternative methods for producing compounds of Formula IV are known in the literature. As illustrated in Equation 5, α-hydroxyhydroxamic acids IV can also be synthesized by treating α-ketohydroxamic acids VII with an excess of a Gregnard reagent. [Geffken, D.; Burchardt, A.; *Arch. Pharm.*, 1988, 321, 311] The reactions are conducted in refluxing ether for 2 to 6 hours.

Equation 5

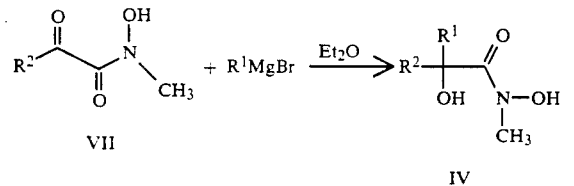

This procedure works best in cases where $R^2$ of the hydroxamic acids VII is a non-enolizable group, for example phenyl.

The α-ketohydroxamic acids VII can be prepared by condensing the glyoxylic acid chlorides VIII, derived from the corresponding carboxylic acids, [Geffken, D.; Burchardt, A.; *Arch. Pham.*, 1988, 321, 311] with O-trimethylsilyl-N-methylhydroxylamine [Geffken, D.; Burchardt, A.; *Arch. Pham.*, 1988, 321, 311] (Equation 6).

Equation 6

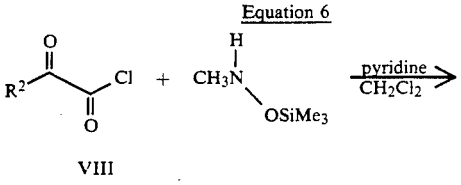

-continued
Equation 6

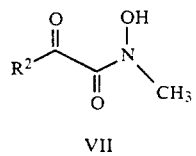

These reactions are conducted in a mixture of pyridine and methylene chloride at 0° C. to 25° C.

The starting α-ketoacids VIII are either purchased from commercial sources or obtained by oxidation of the corresponding methyl ketone with selenium dioxide. [Hallmann, G.; Haegele, K.; *Annalen*, 1963, 662, 147]

A third method for producing α-hydroxyhydroxamic acids IV is specific to examples in which $R^1=R^2$ (IVa). This method, illustrated in Equation 7, involves adding an excess of Grignard reagent, typically five equivalents, to a solution of the hydroxamic acids IX in ether. [Geffken, D., *Arch. Pharm.*, 1987, 320, 382] The reactions are normally performed at reflux.

Equation 7

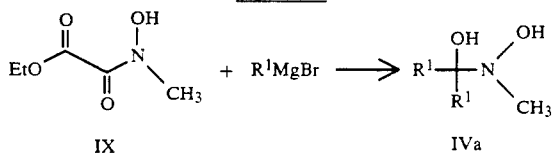

The starting hydroxamic acids IX are prepared by treating ethyl oxalyl chloride X with N-methylhydroxylamine hydrochloride. Sodium carbonate is added as an acid scavenger (Equation 8). [Geffken, D., *Arch. Pharm.*, 1987, 320, 382]

Equation 8

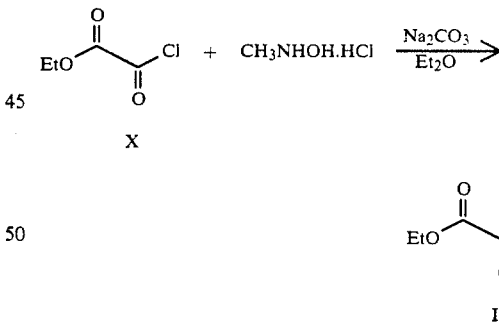

Compounds of general Formula I wherein W and A are O (Ic) are prepared by the method shown in Equation 9.

Equation 9

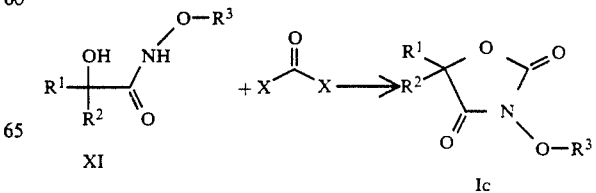

The addition of a carbonylating agent, e.g. phosgene (X=Cl), 1,1'-thiocarbonyldiimidazole (X=imidazole), or oxalyl chloride, to hydroxamic acids of type XI produces dioxotetrahydrooxazoles Ic. The cyclizations can be conducted in an inert solvent, for example benzene or methylene chloride, at temperatures ranging from 0° C. to 80° C. Experimental details for reactions of this type have been reported as have the preparation of the starting hydroxamic acids XI. [Geffken, D.; Zinner, G.; *Chem. Ber.*, 1973, 106, 2246]

Compounds of Formula I in which W is O and A is $NR^4$ (Id) are synthesized by treating hydroxamic acids IIb with various hydrazines, as illustrated in Equation 10. Depending on the nature of the substituents on IIb and the reacting hydrazine, the intermediate N-aminocarbamates XII may or may not be isolated. For cases in which ring closure is not spontaneous under the reaction conditions, treatment of XII with triethylamine in an inert solvent (such as THF) at temperatures ranging from 25° C. to 80° C. induces cyclization to Id. [Geffken, D.; *Arch. Pharm.*, 1982, 315, 802; Geffken, D., *Synthesis*, 1981, 38]

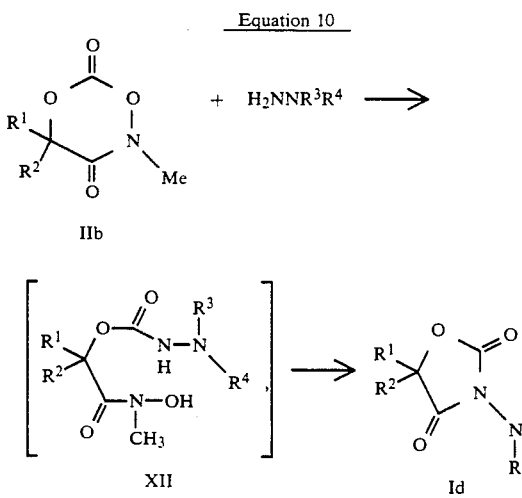

The dioxazinediones IIb are readily prepared from the corresponding α-hydroxyhydroxamic acid by treatment with 1,1'-carbonyldiimidazole (Equation 11). The cyclization is performed in an inert solvent such as methylene chloride and is complete in less than one minute at 25° C. [Geffken, D.; *Arch. Pharm.*, 1982, 315, 802; Geffken, D., *Synthesis*, 1981, 38]

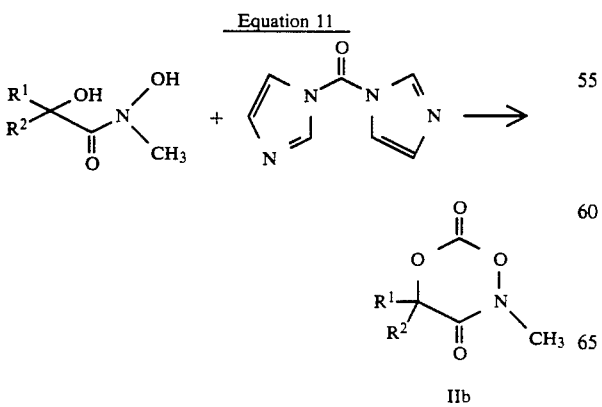

In addition to the methods described above, oxazolidinediones described by Formula I wherein W is O can be prepared by desulfurization of thiooxooxazolidinones as shown in Equation 12.

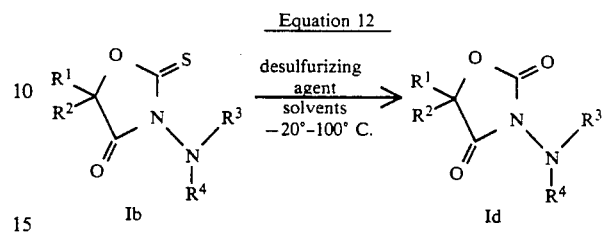

A general procedure for preparing the oxazolidinediones is described below. The thiooxooxazolidinone (Ib) is dissolved in a water-miscible organic solvent such as methanol, acetone, acetonitrile, dimethylformamide, dioxane, tetrahydrofuran, etc. Methanol and acetone are preferred. The solution is treated with a desulfurizing agent such as aqueous OXONE ® ($KHSO_5$), aqueous silver nitrate, bleach (NaOCl), various peroxides and peracids or other reagents known by those skilled in the art to oxidize sulfur. Aqueous OXONE ® and aqueous silver nitrate are preferred. The reaction mixture is stirred at temperatures ranging from about −20° C. to about 100° C. until the reaction is complete.

The product can be isolated by evaporation of the solvent, and purified by washing with water in a water-immiscible solvent such as methylene chloride or ether. Drying, evaporation of the solvent, followed by further purification by recrystallization or chromatography affords pure oxazolidinediones, Id.

A novel process for preparing thiooxooxazolidinones Ib expeditiously and in good yield is also disclosed herein. The process comprises four sequential reactions:

(1) reaction of a 2-hydroxycarboxylic acid ester with a base;

(2) reaction of the product of reaction (1) with carbon disulfide;

(3) reaction of the product of reaction (2) with an acylating agent; and (4) reaction of the product of reaction (3) with a substituted hydrazine.

This sequence of reactions can be conveniently conducted in a single reaction vessel without isolation of chemical intermediates.

The process is represented in Equation 13 for the specific case of preparation of 5-methyl-5-phenyl-3-(phenylamino)-2-thioxo-4-oxazolidinone, and in Equation 14 for the general case:

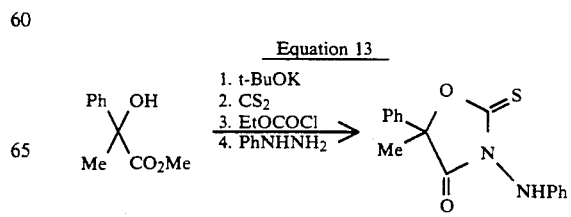

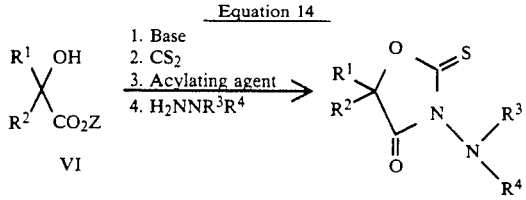

Equation 14
1. Base
2. CS₂
3. Acylating agent
4. H₂NNR³R⁴ wherein for Formula Ib $R^1$ is H; alkyl ($C_1-C_6$); haloalkyl ($C_1-C_6$); cycloalkyl($C_3-C_6$); alkenyl ($C_2-C_6$); alkynyl ($C_2-C_6$); alkoxyalkyl ($C_2-C_6$); alkyl ($C_1-C_3$) substituted with cycloalkyl ($C_3-C_6$); phenyl or benzyl substituted on the ring with $R^6$;

$R^2$ is phenyl substituted with $R^5$ and $R^6$; naphthyl substituted with 1-2 groups selected from $R^6$; thienyl substituted with $R^5$ and $R^6$; furyl substituted with $R^6$; pyridyl substituted with $R^6$, phenoxy or phenylthio; alkyl ($C_1-C_6$); $C_5-C_7$ cycloalkyl;

$R^1$ and $R^2$ can be taken together, along with the carbon atom to which they are attached, to form a carbocyclic or heterocyclic ring (containing O, N-$R^7$, or S) of 5-7 ring atoms. The heterocyclic ring can be fused with an $R^5$-substituted benzene ring or an $R^6$-substituted thiophene ring, the heteroatom not being attached to the spiro center; the carbocyclic ring can be fused with 1-2 $R^5$-substituted benzene rings or with an $R^6$-substituted thiophene ring;

$R^3$ is phenyl substituted with $R^{10}$; benzyl substituted on the benzylic carbon with $R^7$ and on the phenyl ring with $R^{10}$; naphthyl substituted with $R^{10}$; thienyl substituted with $R^{10}$, furyl substituted with $R^{10}$, pyridyl substituted with $R^{10}$, pyridazyl substituted with $R^{10}$, pyrimidyl substituted with $R^{10}$; alkyl ($C_2-C_{10}$); cycloalkyl ($C_5-C_7$);

$R^4$ is H; formyl; alkylcarbonyl ($C_2-C_4$); haloalkylcarbonyl ($C_2-C_4$); alkoxyalkylcarbonyl ($C_2-C_4$); alkoxycarbonyl ($C_2-C_4$); alkylaminocarbonyl ($C_2-C_5$); alkylsulfonyl ($C_1-C_4$); alkyl ($C_1-C_4$); alkenyl ($C_3-C_4$); alkynyl ($C_3-C_4$); cycloalkyl ($C_4-C_6$); phenylaminocarbonyl wherein the phenyl is substituted with $R^{10}$;

$R^3$ and $R^4$ can be taken together, along with the nitrogen atom to which they are attached to form a pyrrolidino, piperidino or pyrrolo ring, which rings can be fused to an $R^{10}$-substituted benzene ring;

$R^5$ is H, halogen; alkyl ($C_1-C_6$); haloalkyl ($C_1-C_4$); alkoxy ($C_1-C_6$); alkenyloxy ($C_3-C_4$); alkylthio ($C_1-C_5$); haloalkylthio ($C_1-C_4$); haloalkyl ($C_1-C_4$); alkylsulfonyl ($C_1-C_4$); haloalkoxy ($C_1-C_4$) alkylsulfonyl ($C_1-C_4$); haloalkylsulfonyl ($C_1-C_4$); nitro; phenyl substituted with $R^6$; phenoxy substituted with $R^6$; phenylthio substituted with $R^6$; cyano; alkynyloxy ($C_3-C_4$); alkoxyalkyl ($C_2-C_6$); alkoxyalkyoxy ($C_2-C_6$); phenoxymethyl with phenyl substituted by $R^6$; benzyloxy with phenyl substituted with $R^6$; phenethyloxy with phenyl substituted by $R^6$; benzyl with phenyl substituted by $R^6$; phenethyl with phenyl substituted by $R^6$; carboalkoxy ($C_2-C_6$); cycloalkyl ($C_5-C_6$);

$R^6$ is H; halogen (1-2); methyl; trifluoromethyl; alkoxy ($C_1-C_4$); methylthio; nitro;

$R^7$ is H; or alkyl ($C_1-C_4$); and $R^{10}$ is 0-2 groups selected from $CF_3$; $CF_3O$; $NO_2$; $CO_2Me$; halogen; $C_1$ to $C_5$ alkyl; $C_1$ to $C_5$ alkoxy; or CN; provided that when the $R^3$ ring is disubstituted, one of the $R^{10}$ alkyl or alkoxy groups is no larger than methyl or methoxy.

The preparation of the α-hydroxyesters VI in Equation 14 is discussed above. The ester group can be alkyl ($C_1-C_{12}$), alkenyl ($C_3-C_4$), cycloalkyl ($C_3-C_{12}$), cycloalkylalkyl ($C_6-C_7$), alkoxyalkyl ($C_2-C_4$) or benzyl. Preferred for ease of synthesis, lower expense or greater utility are esters in which Z is $C_1-C_4$ alkyl.

Thioxooxazolidinones Ib prepared by this method preferred for reasons of ease of synthesis, lower expense or greater utility, are compounds wherein:

$R^1$ is methyl;
$R^2$ is phenyl substituted with $R^5$ and $R^6$;
$R^3$ is phenyl substituted with $R^{10}$; and
$R^4$ is hydrogen.

In each of the reaction steps of Equation 14 it will be understood by those skilled in the art that the optimum combination of reaction time, reaction temperature, stoichiometry, solvent(s), and the like will depend on the exact product being prepared, as well as on the relative importance of these factors and the results to the individual operator. For example:

The reaction time should be sufficient to effect the desired reaction; the reaction temperature should be sufficient to effect the desired reaction in the desired time without undue decomposition or side reactions; the stoichiometry of reactants should generally be the theoretical values, in the interest of economy, with variations as needed to compensate for evaporative or other losses; and solvent(s) can be selected, e.g., so that reaction ingredients have a substantial solubility, in the interest of obtaining relatively fast reaction rates.

In Reaction Step 1—Usable bases are those capable of deprotonation of the hydroxy group without unacceptable side reactions. Included are the alkali metal tertiary alkoxides, hydrides, and hydroxides. Preferred among these in the interest of higher solubility, reactivity, ease or safety of use, higher yields, or economy are the potassium tertiary alkoxides such as potassium tert.-butoxide and potassium tert.-amylate. Especially preferred is potassium tert.-butoxide.

Usable solvents are the 2-hydroxycarboxylic acid ester itself and generally the non-hydroxylic solvents, including ethers (e.g. diethyl ether, tetrahydrofuran, dioxane, 1,2-dimethoxyethane), esters (e.g. methyl and ethyl acetate), amides (e.g. N,N-dimethylformamide, N,N-dimethylacetamide, 1-methyl-2-pyrrolidone), nitriles (e.g. acetonitrile), and the like, and mixtures containing one or more of these solvents. Preferred among these solvents are those in which the reactants have substantial solubility.

The temperature can vary from about −80° C. to about +100° C., with about −20° C. to +80° C. preferred, and with about −5° C. to +50° C. more preferred. Ambient temperature is a convenient temperature at which to conduct the reaction.

The needed reaction time is short with soluble reactants. No more than a few minutes are required at ice to ambient temperatures, e.g. 0.5 to 15 minutes.

In Reaction Step 2, carbon disulfide ($CS_2$) is contacted with the product of Step 1 at about −20° C. to +100° C., preferably −10° C. to +50° C., for about 5 seconds to about 24 hrs., preferably for about 5 to 30 min. The reaction is rapid for soluble reactants. Ambient temperature is a convenient temperature at which to conduct the reaction.

In Reaction Step 3 an acylating agent capable of forming a mixed-anhydride with the product of Reaction Step 2 is contacted with the product of Reaction Step 2. Such acylating agents include chloroformates, e.g. methyl chloroformate, ethyl chloroformate, propyl chloroformate, butyl chloroformate, and benzyl chloroformate, and other acylating agents. Preferred acylating agents are methyl and ethyl chloroformate. The reaction is rapid, and is complete in about 5 seconds to an hour with soluble reactants. Most reactions are complete in about 1 to 30 minutes. The temperature can range from about −20° C. to +50° C. The preferred range is from about −10° C. to +25° C. Ice to ambient temperatures is a convenient temperature range for conducting this reaction.

In Reaction Step 4 the substituted hydrazine reactant is contacted with the product of Reaction Step 3. The substituted hydrazine can be used as the free base or as a mixture of its acid salt with an added acid scavenger such as a tertiary amine base (e.g. triethylamine, N,N-diisopropyl-N-ethylamine). The reaction is rapid, requiring no more than a few minutes for completion with soluble reactants. Reaction times may be 10 seconds to about 1 day, preferably about 1 minutes to 8 hrs. Reaction temperatures can range from about −20° C. to +100° C. Ice to ambient temperatures is a convenient range at which to conduct the reaction.

The product of Step 4 can be isolated by evaporation of the reaction solvent, and it can be purified if desired by dissolving in a water-immiscible solvent (e.g. carbon tetrachloride, butyl chloride, ether), washing with water, mineral acid, and base, followed by drying and evaporation of solvent, in turn followed by crystallization or chromatography as desired.

The compounds that can be made by the process of this invention are described in the Examples and Tables which follow, and are intended to be only exemplary and not all-inclusive.

EXAMPLE 1

Ethyl 2-(3-fluoropyrid-4-yl)lactate

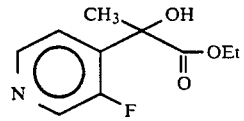

A 27 ml portion of commercially-available 2.03M lithium diisopropylamide-THF/heptane solution (Lithco) was diluted with 50 mL of dry THF, cooled to −60° C. under nitrogen, and stirred while adding a solution of 4.3 mL (4.8 g, 50 mmol) of 3-fluropyridine in 10 mL of dry THF at a rate that held the mixture below −55° C. The resulting slurry was stirred at −60° C. for another 30 minutes, and then with continued cooling and stirring a solution of 6.0 mL (6.4 g, 55 mmol) of ethyl pyruvate in 30 mL of dry THF was added as quickly as possible while maintaining an internal temperature of −60° C. The resulting thin slurry was allowed to come to −10° C., then diluted with 200 mL each of water and ether. The aqueous phase was adjusted to pH 7 by addition of 1N aqueous HCl, the ether phase was separated, the aqueous phase was extracted with two 100 mL portions of ether, and the combined ether phases were washed with three 100-mL portions of water and 100 mL of brine, dried over magnesium sulfate, and evaporated to leave 5.8 g of a dark brown oil. Chromatography over silica gel, eluting with methylene chloride-methanol 99:1, provided 3.7 g (35%) of the title compound as a pale yellow solid: mp 56°-60° C.; IR (Nujol) 2600-3400, 1755, 1730 cm$^{-1}$; NMR (CDCl$_3$, 200 MHz) 1.2 (3H, t, J=7), 1.8 (3H, s), 3.9 (1H, s), 4.3 (2H, q, J=7), 7.5 (1H d of d, J=5,7), 8.4-8.5 (2H, m).

EXAMPLE 2

Ethyl 2-(4-phenoxyphenyl)lactate

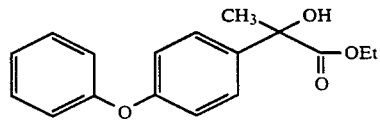

A 250-ml flask fitted with magnetic stirring, water condenser, 125 mL dropping funnel, thermometer, and nitrogen inlet was charged with 2.7 g (110 mmol) of magnesium metal and dried with a heat gun under strong nitrogen purge. After cooling, the funnel was charged with a solution of 17.5 mL (24.9 g, 100 mmol) of 4-bromodiphenyl ether in 67 mL of dry THF, and 10 mL was run into the flask. With stirring, the Grignard initiated spontaneously, and the rest of the bromide solution was added over 15 minutes, maintaining an internal temperature of 67°-68° C. When addition was complete, the temperature held at 68° C. for 5 minutes, then began to drop, reaching 30° C. after 45 minutes.

Meanwhile, a 250 mL flask, magnetic stirrer, and 125 mL dropping funnel that had been oven dried were assembled hot under nitrogen and allowed to cool. A low-temperature thermometer was then added, the flask was charged with a solution of 11.5 mL (12.2 g, 105 mmol) of ethyl pyruvate in 66 mL of dry THF, and the solution of Grignard reagent was transferred to the dropping funnel by means of a syringe. The pyruvate solution was chilled to −10° C., and the Grignard solution was run in over 15 minutes with good stirring, cooling to maintain an internal temperature of −5° C. to −10° C.

The resulting solution was stirred and treated with 50 mL of water followed by 50 mL of saturated aqueous ammonium chloride, giving two clear phases. These were separated, and the upper phase was subjected to rotary evaporation to remove most of the THF. Addition of 50-mL portions of water and methylene chloride gave two clear phases.

These were separated, the aqueous phase was washed with another 25 mL of methylene chloride, and the combined organic phases were washed with water and brine, dried over magnesium sulfate,, and evaporated to leave 23.8 g of yellow-orange oil. Kugelrohr distillation at 140° C./0.1-0.2 mm for 60 minutes removed volatile impurities, leaving 17.1 g (60%) of the product as a clear orange oil: n$_D$26 1.5555; IR (neat) 3490, 1725 cm$^{-1}$; NMR (CDCl$_3$, 200 MHz) 1.3 (3H, t, J=7), 1.8 (3H, s), 3.8 (1H, broad s), 4.2 (2H, m), 6.9-7.0 (4H, m), 7.1 (1H, t, J=7), 7.3 (2H, t, J=7), 7.5 (2H, d, J=9).

EXAMPLE 3

Preparation of
5-Methyl-5-phenyl-3-(phenylamino)-2-thioxo-4-oxazolidinone

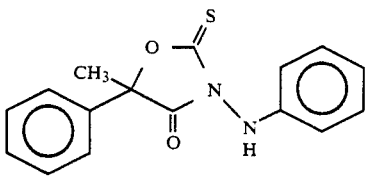

A solution of methyl atrolactate (7.64 g, 0.0424 mole) in tetrahydrofuran (80 ml) was stirred and cooled in an ice bath, and potassium tert.-butoxide (4.76 g, 0.0424 mole) was added. The ice bath was removed, and the mixture was stirred for 10 minutes. This procedure provided a clear, yellow solution at 21° C.

Carbon disulfide (2.8 ml, 0.046 mole) was added, and caused the formation of an orange color and a temperature rise to 32° C. The solution was cooled in an ice bath for 10 minutes, causing the temperature to fall to 4° C.

Ethyl chloroformate (4.1 ml, 0.043 mole) was added to the ice-cooled solution, inducing the formation of a turbid yellow mixture and a temperature rise to 12° C. The mixture was stirred with ice-bath cooling for 5 minutes as the temperature fell to 5° C.

Phenylhydrazine (97%, 4.5 ml, 0.044 mole) was added. The temperature rose to 24° C. while the cooling bath was applied. After the temperature fell to 20° C., the mixture was stirred for 10 minutes, then evaporated under reduced pressure to an oil.

The oil was mixed with 1-chlorobutane and water, and the layers were separated. The organic layer was washed with 1N HCl, water, and saturated aq. sodium bicarbonate solution. The organic solution was dried (magnesium sulfate), filtered, and evaporated under reduced pressure to an oil. The oil was crystallized from carbon tetrachloride/hexane (~40 ml/20 ml), providing the product (7.40 g, 58.5% of theory) as a light-yellow solid, m.p. 104°-105° C. The product was further purified by recrystallization from carbon tetrachloride/hexane with 93% recovery.

In another preparation of the same product, carbon tetrachloride was used instead of 1-chlorobutane during the workup. Crystallization from the carbon tetrachloride solution by dilution with hexane provided the product in 54% yield. Recrystallization from isopropanol/water provided the product as a white solid, m.p. 108°-109° C., with 97% recovery.

EXAMPLE 4

Preparation of
5-Phenyl-3-(phenylamino)-2-thioxo-4-oxazolidinone

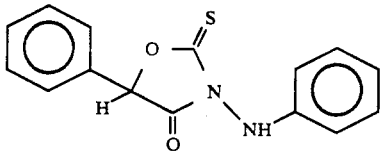

A stirred solution of potassium tert.-butoxide (11.22 g, 0.1 mole) in tetrahydrofuran (100 ml), held at 0° C. to −5° C., was treated portionwise with a solution of methyl mandelate (16.62 g, 0.1 mole) in tetrahydrofuran (70 ml), providing an orange-red solution. After 4 minutes carbon disulfide (6.04 ml, 0.1 mole) was added. After 5 minutes at 0° C. to −5° C., the orange solution was cooled to −30° C. and treated with ethyl chloroformate (9.5 ml, 0.1 mole). After 2 minutes the solution was warmed to −10° C. After 5 minutes at −10° C., the solution was cooled to −30° C. and treated with 97% phenylhydrazine (10.1 ml, 0.1 mole). The yellow solution was warmed to 25° C., and after 10 minutes the mixture was evaporated under reduced pressure to a turbid oil. The oil was mixed with water and 1-chlorobutane, the layers were separated, and the organic solution was washed with 1N HCl, water (twice), and saturated sodium bicarbonate solution. The dried (magnesium sulfate) solution was evaporated under reduced pressure to a yellow-orange oil, and the oil was dissolved in chloroform. A silica-gel filtration of the chloroform solution followed by evaporation of the filtrate under reduced pressure provided a green oil which began to solidify. Further purification was accomplished by crystallization from 1-chlorobutane. This procedure provided the product as 9.9 g (35% of theoretical) of a white solid, m.p. 140°-141° C. The infrared spectrum (Nujol mull) showed the characteristic absorption at 3295 cm$^{-1}$ (N-H) and 1760 cm$^{-1}$ (imide C=O).

EXAMPLE 5

Preparation of
3'-(Phenylamino)-2'-thioxo-spiro(9H-fluorene-9,5'-oxazolidin)-4'-one

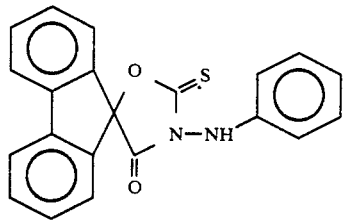

A solution of 9-hydroxy-9-fluorenecarboxylic acid, methyl ester (8.91 g, 0.0371 mole) in tetrahydrofuran (89 ml) was treated with potassium tert.-butoxide (4.16 g, 0.0371 mole). After 6 minutes the solution was cooled in an ice bath and carbon disulfide (2.3 ml, 0.038 mole) was added. After 7 minutes ethyl chloroformate (3.6 ml, 0.038 mole) was added to the cold solution. After 7 minutes 97% phenylhydrazine (3.9 ml, 0.038 mole) was added. After 3 minutes, the mixture was evaporated under reduced pressure to a yellow syrup. The syrup was treated with 1-chlorobutane and water, and the organic layer was washed with saturated sodium bicarbonate solution, water, 1N HCl, and water. The dried (magnesium sulfate) solution was filtered and evaporated under reduced pressure to an oil. The oil was crystallized from carbon tetrachloride/hexane, and the solid product further purified by boiling with isopropanol (without dissolution of all solid), cooling, and filtering. The product was obtained as 3.56 g (27% of theoretical) of analytically-pure white solid, m.p. 187°-189° C.

Anal. Calcd. for $C_{21}H_{14}N_2O_2S$: C, 70.37; H, 3.94; N, 7.82%. Anal. Found: C, 70.28; H, 4.19; N, 7.68%. The infrared spectrum (Nujol mull) showed absorption at 3275 cm$^{-1}$ (N-H) and 1770 cm$^{-1}$ (imide C=O).

EXAMPLE 6

5-(3-Fluoropyrid-4-yl)-5-methyl-3-phenylamino-2-thioxo-4-oxazolidinone

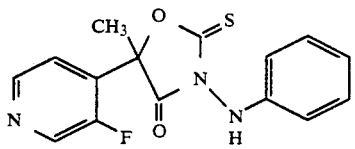

A solution of 3.2 g (15 mmol) of ethyl 2-(3-fluoropyrid-4-yl)lactate in 20 mL of THF was stirred and chilled in an ice-water bath while 1.6 g (15 mmol) of solid potassium tertiary-butoxide was added in portions. The cooling bath was then removed, 1.0 mL (1.2 g, 15.5 mmol) of carbon disulfide was added, the mixture was stirred for 10 minutes, cooling was resumed, 1.4 mL (1.6 g, 15 mmol) of ethyl chloroformate was added, the mixture was stirred for 10 minutes, 1.5 mL (15 mmol) of phenylhydrazine was added, the resulting slurry was stirred and allowed to come to room temperature, another 20 mL of THF was added, and the mixture was stirred another 15 minutes at room temperature. Most of the solvent was then removed by rotary evaporation, the residue was partitioned between 1-chlorobutane and water, and the organic phase was separated, washed with 0.1N aqueous HCl, water, saturated aqueous sodium bicarbonate, water, and brine, dried over magnesium sulfate, and evaporated to leave 3.7 g of a green gum. Chromatography over silica gel, eluting with methylene chloride:methanol 98:2, provided 1.7 g (35%) of the title compound as a semisolid. Crystallization from ethyl acetate-hexanes 1:1 gave pale yellow crystals: mp 165°-169° C.; IR (Nujol) 3200, 3130, 1780 cm$^{-1}$; NMR (CDCl$_3$, 200 MHz) 2.2 (3H, s), 6.4 (1H, s), 6.8 (2H, d, J=8), 7.0 (1H, t, J=8), 7.3 (2H, t, J=8), 7.5 (1H, t, J=6), 8.6 (2H, m).

Applying a similar procedure to ethyl 2-(2-fluoropyrid-3-yl)acetate gave 5-(2-fluoropyrid-3-yl)-5-methyl-3-phenylamino-2-thioxo-4-oxazolidinone, mp 130°-135° C.

EXAMPLE 7

(S)-5-Methyl-5-phenyl-3-phenylamino-2-thioxo-4-oxazolidinone

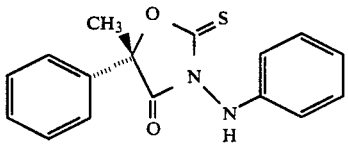

A solution of 1.0 g (6.0 mmol) of (S)-atrolactic acid in 7 mL of methanol was cooled in an ice-water bath and stirred while 0.70 mL (1.15 g, 9.6 mmol) of thionyl chloride was added dropwise. The resulting mixture was stirred at room temperature for one hour, then concentrated under reduced pressure to give 1.1 g of methyl (S)-atrolactate, n$_D$25 1.5096.

This material was dissolved in 10 mL of THF, and the solution was stirred and chilled in an ice-water bath while 0.68 g (6.1 mmol) of solid potassium teritary-butoxide was added in one portion. The resulting slurry was stirred at room temperature for 40 minutes, then 0.40 mL (0.51 g, 6.7 mmol) of carbon disulfide was added, giving a solution. Ice-water cooling was resumed, and after 10 minutes 0.58 mL (0.66 g, 6.1 mmol) of ethyl chloroformate was added, giving a slurry.

After another 5 minutes 0.60 mL (0.66 g, 6.1 mmol) of phenyl hydrazine was added, cooling was removed, and the mixture was allowed to come to room temperature. Most of the THF was removed under reduced pressure, the residue was partitioned between water and 1-chlorobutane, and the organic phase was washed sequentially with 1N aqueous HCl, water, saturated aqueous sodium bicarbonate, and brine, dried over magnesium sulfate, and evaporated to leave 1.4 g of an oil. Chromatography over silica gel, eluting with methylene chloride-hexanes 70:30, provided 0.89 g (50%) of the title compound as an oil that slowly solidified on standing. Crystallization from 1-chlorobutane-hexanes 5:3 gave colorless needles: mp 81°-85° C.; [α]$_D$23 +70.1 (c=0.52, EtOH); IR (Nujol) 3250, 1775 cm$^{-1}$; NMR (CDCl$_3$, 200 MHz) 2.05 (3H, s), 6.37 (1H, s), 6.73 (2H, d, J=8), 7.02 (1H, t, J=8), 7.24 (2H, t, J=8), 7.4-7.5 (3H, m), 7.5-7.6 (2H, m).

Applying similar procedures to (R)-atrolactic acid gives (R)-3-(phenylamino)-5-phenyl-5-methyl-2-thioxo-4-oxazolidinone; mp 81°-85° C.; [α]$_D$23 −70.5 (c=0.52, EtOH).

EXAMPLE 8

Preparation of 5-Methyl-5-(4-phenoxyphenyl)-3-(phenylamino)-2,4-oxazolidinedione

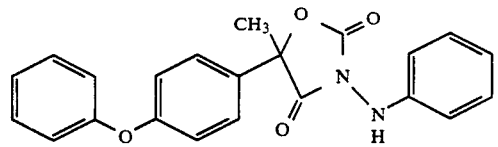

A solution of 5-methyl-5-(4-phenoxyphenyl)-3-phenylamino-2-thioxooxazolidin-4-one (2 g, 0.0051 moles) in 50 mls of acetone (0.1M) was treated at room temperature with a solution of KHSO$_5$ OXONE®, 4.72 g, 0.0154 moles) in 20 mls of water. The white slurry was heated at 50° C. for two hours then cooled to room temperature and filtered. The residue was washed with fresh acetone and the filtrates were evaporated under reduced pressure until all the acetone distilled away. The residue was dissolved in methylene chloride and washed with water and brine. The organic layer was dried (MgSO$_4$), filtered, and evaporated to give the crude product. Recrystallization from 1-chlorobutane and petroleum ether afforded 1.68 g (88% of theoretical) of pure product as a white solid with a melting point of 140°-142° C.

Tables I and II on the following pages show fungicidal compounds that can be advantageously prepared by the methods described above. These tables are illustrative of the invention only, and are not intended to be inclusive.

TABLE 1

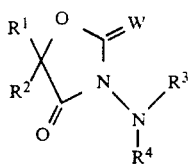

| EX # | W | R¹ | R² | R³ | R⁴ | mp(°C.) |
|---|---|---|---|---|---|---|
| 1 | S | Me | Ph | Ph | H | 109[1] |
| 2 | S | Me | Ph | Ph | H | 87[2] |
| 3 | S | Me | Ph | Ph | H | 87[3] |
| 4 | S | H | Ph | Ph | H | 142 |
| 5 | S | Et | Ph | Ph | H | 96 |
| 6 | S | n-hexyl | Ph | Ph | H | |
| 7 | S | n-butyl | Ph | Ph | H | 100 |
| 8 | S | CF₃ | Ph | Ph | H | |
| 9 | S | CF₃CH₂CH₂CH₂ | Ph | Ph | H | |
| 10 | S | cyclopropyl | Ph | Ph | H | 98 |
| 11 | S | cyclobutyl | Ph | Ph | H | oil |
| 12 | S | cyclohexyl | Ph | Ph | H | |
| 13 | S | vinyl | Ph | Ph | H | 107 |
| 14 | S | allyl | Ph | Ph | H | 113 |
| 15 | S | acetylenyl | Ph | Ph | H | |
| 16 | S | propargyl | Ph | Ph | H | |
| 17 | S | methoxymethyl | Ph | Ph | H | |
| 18 | S | cyclopropylmethyl | Ph | Ph | H | |
| 19 | S | benzyl | Ph | Ph | H | 116 |
| 20 | S | 4'-methoxybenzyl | Ph | Ph | H | |
| 21 | S | 4'-nitrobenzyl | Ph | Ph | H | |
| 22 | S | 4'-trifluoro-methylbenzyl | Ph | Ph | H | |
| 23 | S | 4'-methylbenzyl | Ph | Ph | H | |
| 24 | S | 2',4'-dichloro-benzyl | Ph | Ph | H | |
| 25 | S | 4'-fluorobenzyl | Ph | Ph | H | |
| 26 | S | Me | 4-n-octylphenyl | Ph | H | |
| 27 | S | Me | 4-(2-octenyloxy)phenyl | Ph | H | |
| 28 | S | Me | 4-(2-propenyl)phenyl | Ph | H | |
| 29 | S | Me | 4-(2-octenyl)phenyl | Ph | H | |
| 30 | S | Me | 4-n-octylthiophenyl | Ph | H | |
| 31 | S | Me | 4-(1,1-dichloroallyl-phenyl | Ph | H | |
| 32 | S | Me | 4-(2-butynyl)phenyl | Ph | H | |
| 33 | S | H | Me | Ph | H | 117 |
| 34 | S | H | t-Bu | Ph | H | 98 |
| 35 | S | H | i-Pr | Ph | H | 107 |
| 36 | S | H | cyclohexyl | Ph | H | 90 |
| 37 | S | Me | Me | Ph | H | 132 |
| 38 | S | benzyl | Me | Ph | H | 99 |
| 39 | S | Me | phenoxymethyl | Ph | H | 77 |
| 40 | S | Me | n-hexyl | Ph | H | |
| 41 | S | Me | cyclohexyl | Ph | H | oil |
| 42 | S | Me | 4-chlorophenyl | Ph | H | 156 |
| 43 | S | Me | 3-chlorophenyl | Ph | H | 105 |
| 44 | S | Me | 2-chlorophenyl | Ph | H | 170 |
| 45 | S | Me | 4-fluorophenyl | Ph | H | 150 |
| 46 | S | Me | 3-fluorophenyl | Ph | H | 108 |
| 47 | S | Me | 4-bromophenyl | Ph | H | 115 |
| 48 | S | Me | 3,5-dichloro-phenyl | Ph | H | |
| 49 | S | Me | 3,4-dichloro-phenyl | Ph | H | 143 |
| 50 | S | Me | 2,4-dichloro-phenyl | Ph | H | 161 |
| 51 | S | Me | 2-fluorophenyl | Ph | H | 123 |
| 52 | S | Et | 2-fluorophenyl | Ph | H | 130 |
| 53 | S | H | 2-fluorophenyl | Ph | H | |
| 54 | S | vinyl | 2-fluorophenyl | Ph | H | 102 |
| 55 | S | Me | 2-fluorophenyl | 4-fluoro-phenyl | H | 129 |
| 56 | S | Me | 2-fluorophenyl | 2-methyl-phenyl | H | 129 |
| 57 | S | Me | 2-fluorophenyl | 4-methyl-phenyl | H | 140 |
| 58 | S | Me | 2-fluorophenyl | 2,6-di-chlorophenyl | H | 148 |
| 59 | S | Me | 2-fluorophenyl | Ph | Me | 134 |
| 60 | S | Me | 2,3-difluoro-phenyl | Ph | H | 120 |
| 61 | S | Me | 2,5-difluoro- | Ph | H | 119 |

TABLE 1-continued $$\underset{R^2}{\overset{R^1}{\diagdown}}\underset{\underset{O}{\|}}{C}\underset{N}{\overset{O}{\diagdown}}\underset{\underset{R^4}{|}}{N}\underset{R^3}{\diagup}$$

| EX # | W | R¹ | R² | R³ | R⁴ | mp(°C.) |
|------|---|-----|-----|-----|-----|---------|
| 62 | S | Me | 3,5-difluorophenyl | Ph | H | 135 |
| 63 | S | Me | 2,6-difluorophenyl | Ph | H | 137 |
| 64 | S | Me | 3,4-difluorophenyl | Ph | H | 97 |
| 65 | S | Me | 2,4-difluorophenyl | Ph | H | 127 |
| 66 | S | Et | 2,4-difluorophenyl | Ph | H | |
| 67 | S | H | 2,4-difluorophenyl | Ph | H | |
| 68 | S | vinyl | 2,4-difluorophenyl | Ph | H | |
| 69 | S | Me | 2,4-difluorophenyl | Ph | Me | 128 |
| 70 | S | Me | 2,4-difluorophenyl | 2,6-dichlorophenyl | H | 185 |
| 71 | S | Me | 2,4-difluorophenyl | 4-fluorophenyl | H | 136 |
| 72 | S | Me | 2,4-difluorophenyl | 4-methylphenyl | H | 134 |
| 73 | S | Me | 2,4-difluorophenyl | 2-methylphenyl | H | |
| 74 | S | H | 2-methylphenyl | Ph | H | 121 |
| 75 | S | Me | 2-methylphenyl | Ph | H | 115 |
| 76 | S | Me | 4-methylphenyl | Ph | H | 108 |
| 77 | S | Me | 2,5-dimethylphenyl | Ph | H | |
| 78 | S | Me | 4-t-butylphenyl | Ph | H | 124 |
| 79 | S | Me | 4-cyclohexylphenyl | Ph | H | 160 |
| 80 | S | Me | 3-trifluoromethylphenyl | Ph | H | 133 |
| 81 | S | Me | 3-nonafluorobutylphenyl | Ph | H | |
| 82 | S | Me | 2-methoxyphenyl | Ph | H | |
| 83 | S | Me | 4-methoxyphenyl | Ph | H | 156 |
| 84 | S | Me | 4-ethoxyphenyl | Ph | H | 64 |
| 85 | S | Me | 4-n-pentyloxyphenyl | Ph | H | 79 |
| 86 | S | Me | 4-allyloxyphenyl | Ph | H | |
| 87 | S | Me | 3-methylthiophenyl | Ph | H | |
| 88 | S | Me | 4-trifluoromethylthiophenyl | Ph | H | |
| 89 | S | Me | 4-trifluoromethoxyphenyl | Ph | H | |
| 90 | S | Me | 2-cyanophenyl | Ph | H | |
| 91 | S | Me | 4-cyanophenyl | Ph | H | |
| 92 | S | Me | 2-n-pentyloxyphenyl | Ph | H | 146 |
| 93 | S | Me | 3-n-pentyloxyphenyl | Ph | H | 67 |
| 94 | S | Me | 4-dimethylaminophenyl | Ph | H | |
| 95 | S | Me | 4-(N-methyl-N-phenylamino)phenyl | Ph | H | |
| 96 | S | Me | 4-phenoxyphenyl | Ph | H | 115 |
| 97 | S | Et | 4-phenoxyphenyl | Ph | H | |
| 98 | S | H | 4-phenoxyphenyl | Ph | H | |
| 99 | S | Me | 4-phenoxyphenyl | Ph | Me | 75 |
| 100 | S | Me | 4-phenoxyphenyl | 2-methylphenyl | H | 139 |
| 101 | S | Me | 4-phenoxyphenyl | 4-methylphenyl | H | |
| 102 | S | Me | 4-phenoxyphenyl | 4-fluorophenyl | H | |
| 103 | S | Me | 3-phenoxyphenyl | Ph | H | oil |
| 104 | S | Me | 2-phenoxyphenyl | Ph | H | 156 |
| 105 | S | Me | 4-(4-chloro- | Ph | H | 114 |

TABLE 1-continued

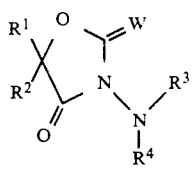

| EX # | W | R¹ | R² | R³ | R⁴ | mp(°C.) |
|---|---|---|---|---|---|---|
| 106 | S | Me | 4-(4-bromophenoxy)phenyl | Ph | H | 111 |
| 107 | S | Me | 4-(4-fluorophenoxy)phenyl | Ph | H | 137 |
| 108 | S | Me | 4-(3-fluorophenoxy)phenyl | Ph | H | 88 |
| 109 | S | Me | 4-(2-fluorophenoxy)phenyl | Ph | H | |
| 110 | S | Me | 4-(4-nitrophenoxy)phenyl | Ph | H | 61 |
| 111 | S | Me | 4-(4-methylphenoxy)phenyl | Ph | H | |
| 112 | S | Me | 4-(2-methylphenoxy)phenyl | Ph | H | oil |
| 113 | S | Me | 4-benzyloxyphenyl | Ph | H | 157 |
| 114 | S | Me | 2-fluoro-4-phenoxyphenyl | Ph | H | 114 |
| 115 | S | Me | 4-carbomethoxyphenyl | Ph | H | |
| 116 | S | Me | 4-carbophenoxyphenyl | Ph | H | |
| 117 | S | Me | 3-pyridyl | Ph | H | |
| 118 | S | Me | 4-pyridyl | Ph | H | |
| 119 | S | Me | 4-fluoro-3-pyridyl | Ph | H | |
| 120 | S | Me | 3-fluoro-2-pyridyl | Ph | H | |
| 121 | S | H | 3-(3,5-dichlorophenoxy)phenyl | Ph | H | 130 |
| 122 | S | H | 3-(3-trifluoromethylphenoxy)phenyl | Ph | H | oil |
| 123 | S | H | 3-phenoxyphenyl | Ph | H | 136 |
| 124 | S | Me | 4-(4-trifluoromethylphenoxy)phenyl | Ph | H | |
| 125 | S | Me | 4-(4-methoxyphenoxy)phenyl | Ph | H | oil |
| 126 | S | Me | 4-(2,4-dichlorophenoxy)phenyl | Ph | H | 121 |
| 127 | S | Me | 4-methanesulfonylphenyl | Ph | H | |
| 128 | S | Me | 4-nitrophenyl | Ph | H | 170 |
| 129 | S | Me | 3-trifluoromethylphenyl | Ph | H | 134 |
| 130 | S | Me | 4-phenylthiophenyl | Ph | H | 144 |
| 131 | S | Me | 4-phenylphenyl | Ph | H | 172 |
| 132 | S | Me | 2-naphthyl | Ph | H | 152 |
| 133 | S | Me | 1-naphthyl | Ph | H | 139 |
| 134 | S | Me | 2-thienyl | Ph | H | |
| 135 | S | Me | 5-chloro-2-thienyl | Ph | H | |
| 136 | S | Me | 4,5-dichloro-2-thienyl | Ph | H | 132 |
| 137 | S | Me | 5-methyl-2-thienyl | Ph | H | |
| 138 | S | Me | 3-methoxy-2-thienyl | Ph | H | |
| 139 | S | Me | 3-thienyl | Ph | H | 121 |
| 140 | S | Me | 2,5-dichloro-3-thienyl | Ph | H | 146 |
| 141 | S | Me | 2,5-dimethyl-3-thienyl | Ph | H | 88 |
| 142 | S | Me | 2-phenoxy-3-thienyl | Ph | H | |
| 143 | S | Me | 2-nitro-4-thienyl | Ph | H | |
| 144 | S | Me | 3-methoxy-4-thienyl | Ph | H | |
| 145 | S | Me | 2-furyl | Ph | H | |
| 146 | S | Me | 3-furyl | Ph | H | |
| 147 | S | Me | 2-pyridyl | Ph | H | |
| 148 | S | Me | 5-fluoro-3-pyridyl | Ph | H | |
| 149 | S | Me | 2-fluoro-3-pyridyl | Ph | H | 134 |
| 150 | S | Me | 2-fluoro-4-pyridyl | Ph | H | |
| 151 | S | Me | 3-fluoro-4-pyridyl | Ph | H | 168 |
| 152 | S | | —CH₂(CH₂)₃CH₂— | Ph | H | oil |
| 153 | S | | —CH₂(CH₂)₃CH₂— | 3,5-dichlorophenyl | H | 184 |
| 154 | S | | —CH₂CH₂NMeCH₂CH₂— | Ph | H | |
| 155 | S | | —CH₂CH₂SCH₂CH₂— | Ph | H | |

TABLE 1-continued $$\underset{R^2}{\overset{R^1}{\diagdown}}\underset{\|}{C}\underset{O}{\overset{O}{\diagup}}\underset{\underset{R^4}{|}}{\overset{\|}{N}}\underset{R^3}{\overset{W}{\diagdown}}$$

| EX # | W | R¹ | R² | R³ | R⁴ | mp(°C.) |
|---|---|---|---|---|---|---|
| 156 | S | | (indanyl-CH₂) | Ph | H | 168 |
| 157 | S | | (tetrahydronaphthyl) | Ph | H | |
| 158 | S | | (thienyl-propyl) | Ph | H | |
| 159 | S | Me | 4-carbomethoxy-phenyl | Ph | H | |
| 160 | S | Me | 4-benzyl-phenyl | Ph | H | 104 |
| 161 | S | | (biphenyl) | Ph | H | 189 |
| 162 | S | Me | Ph | 3,5-dichlorophenyl | H | 142 |
| 163 | S | cyclopropyl | Ph | 3,5-dichlorophenyl | H | 133 |
| 164 | S | Me | phenoxymethyl | 3,5-dichlorophenyl | H | 146 |
| 165 | S | Me | Ph | 2,6-dichlorophenyl | H | 157 |
| 166 | S | Me | 4-phenoxyphenyl | 2,6-dichlorophenyl | H | 118 |
| 167 | S | Me | phenoxymethyl | 2,6-dichlorophenyl | H | 122 |
| 168 | S | H | t-Bu | 2,6-dichlorophenyl | H | 87 |
| 169 | S | Me | Ph | 4-fluorophenyl | H | 72 |
| 170 | S | Me | 4-fluorophenyl | 4-fluorophenyl | H | 91 |
| 171 | S | Me | 4-cyclohexyl-phenyl | 4-fluorophenyl | H | 155 |
| 172 | S | Me | phenylthiomethyl | 4-fluorophenyl | H | 68 |
| 173 | S | Me | Ph | 3-fluorophenyl | H | 70 |
| 174 | S | Me | Ph | 4-chlorophenyl | H | |
| 175 | S | Me | Ph | 3-chlorophenyl | H | 132 |
| 176 | S | Me | Ph | 2-chlorophenyl | H | 121 |
| 177 | S | Me | Ph | 2-fluorophenyl | H | oil |
| 178 | S | Me | Ph | 2,5-difluorophenyl | H | oil |
| 179 | S | Me | Ph | 2-bromophenyl | H | 120 |
| 180 | S | Me | Ph | 4-methylphenyl | H | 142 |
| 181 | S | Me | 4-fluorophenyl | 4-methylphenyl | H | 106 |
| 182 | S | Me | 4-phenoxyphenyl | 4-methylphenyl | H | 146 |
| 183 | S | Me | phenylthiomethyl | 4-methylphenyl | H | 89 |
| 184 | S | Me | phenoxymethyl | 4-methylphenyl | H | 155 |
| 185 | S | Me | 2,5-dichloro-3-thienyl | 4-methylphenyl | H | 145 |
| 186 | S | Me | Ph | 2,6-dimethylphenyl | H | 101 |
| 187 | S | Me | Ph | 4-t-butylphenyl | H | 125 |
| 188 | S | Me | Ph | 3-methylphenyl | H | 97 |
| 189 | S | Me | Ph | 2-methylphenyl | H | 100 |
| 190 | S | Me | Ph | 2-methoxyphenyl | H | 110 |
| 191 | S | Me | Ph | 4-methoxyphenyl | H | 135 |
| 192 | S | Me | Ph | 3-methoxyphenyl | H | oil |
| 193 | S | Me | Ph | 4-n-pentyloxyphenyl | H | oil |

TABLE 1-continued

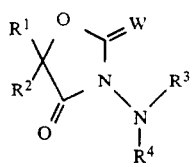

| EX # | W | R¹ | R² | R³ | R⁴ | mp(°C.) |
|---|---|---|---|---|---|---|
| 194 | S | Me | Ph | 4-allyloxyphenyl | H | |
| 195 | S | Me | Ph | 4-trifluoro-methoxyphenyl | H | 73 |
| 196 | S | Me | Ph | 4-trifluoromethyl-phenyl | H | |
| 197 | S | Me | Ph | 3-trifluoromethyl-phenyl | H | |
| 198 | S | Me | Ph | 2-trifluoromethyl-phenyl | H | 115 |
| 199 | S | Me | Ph | 2-nitrophenyl | H | 137 |
| 200 | S | Me | Ph | 4-nitrophenyl | H | |
| 201 | S | Me | Ph | 4-cyanophenyl | H | |
| 202 | S | Me | Ph | 4-carbomethoxy-phenyl | H | 151 |
| 203 | S | Me | Ph | benzyl | H | 82 |
| 204 | S | Me | Ph | 2-thienyl | H | |
| 205 | S | Me | Ph | 3-furyl | H | |
| 206 | S | Me | Ph | 2-pyridyl | H | 147 |
| 207 | S | Me | Ph | 5-trifluoromethyl-2-pyridyl | H | 150 |
| 208 | S | Me | Ph | 2-pyrimidyl | H | 187 |
| 209 | S | Me | Ph | 6-chloro-3-pyridazyl | H | 184 |
| 210 | S | Me | Ph | ethyl | H | |
| 211 | S | Me | Ph | cyclohexyl | H | |
| 212 | S | Me | Ph | t-Bu | H | 48 |
| 213 | S | Me | Ph | n-hexyl | H | oil |
| 214 | S | Me | Ph | n-decyl | H | |
| 215 | S | Me | Ph | Ph | formyl | |
| 216 | S | Me | Ph | Ph | acetyl | 96 |
| 217 | S | Me | Ph | Ph | trifluoro-acetyl | 62 |
| 218 | S | Me | Ph | Ph | methoxy-acetyl | oil |
| 219 | S | Me | Ph | Ph | methoxy-carbonyl | |
| 220 | S | Me | Ph | Ph | methylamino-carbonyl | |
| 221 | S | Me | Ph | Ph | methane-sulfonyl | |
| 222 | S | Me | 3-thienyl | Ph | methyl | 82 |
| 223 | S | 4-fluoro-phenyl | Ph | Ph | methyl | 118 |
| 224 | S | Me | Ph | Ph | methyl | 62 |
| 225 | S | Me | Ph | Ph | phenylamino-carbonyl | |
| 226 | S | Me | Ph | 2-methyl-phenyl | methyl | oil |
| 227 | S | Me | 2,5-dichloro-3-thienyl | Ph | methyl | 147 |
| 228 | S | Me | 4,5-dichloro-2-thienyl | Ph | methyl | 146 |
| 229 | S | Me | Ph | Ph | ethyl | oil |
| 230 | S | Me | Ph | Ph | n-pentyl | |
| 231 | S | Me | 3-thienyl | 4-fluoro-phenyl | H | |
| 232 | S | Me | 3-thienyl | 4-fluoro-phenyl | acetyl | |
| 233 | S | Me | Ph | Ph | allyl | |
| 234 | S | Me | Ph | Ph | propargyl | |
| 235 | S | Me | Ph | Ph | cyclobutyl | |
| 236 | S | Me | Ph | Ph | benzyl | |
| 237 | S | Me | Ph | | 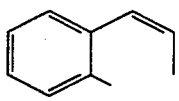 | 161 |
| 238 | S | Me | Ph | Ph | 2-bromo-propionyl | oil |

TABLE 1-continued

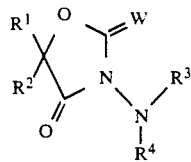

| EX # | W | R¹ | R² | R³ | R⁴ | mp(°C.) |
|---|---|---|---|---|---|---|
| 239 | S | Me | Ph | Ph | bromo-acetyl | 112 |
| 240 | S | Me | 2,5-di-chloro-3-thienyl | Ph | methoxy-acetyl | 82 |
| 241 | S | Me | 4,5-dichloro-2-thienyl | Ph | methoxy-acetyl | 80 |
| 242 | S | Me | Ph | 1-pyrrolo | | 80 |
| 243 | S | Me | 4-fluoro-phenyl | 1-pyrrolo | | 118 |
| 244 | S | Me | 4-cyclohexyl-phenyl | 1-pyrrolo | | 112 |
| 245 | S | Me | 3-thienyl | 1-pyrrolo | | 84 |
| 246 | O | Me | Ph | Ph | H | 163[4] |
| 247 | O | Me | Ph | Ph | H | 92[5] |
| 248 | O | H | Ph | Ph | H | |
| 249 | O | Et | Ph | Ph | H | |
| 250 | O | n-hexyl | Ph | Ph | H | |
| 251 | O | CF₃ | Ph | Ph | H | |
| 252 | O | CF₃CH₂CH₂CH₂ | Ph | Ph | H | |
| 253 | O | cyclopropyl | Ph | Ph | H | |
| 254 | O | cyclohexyl | Ph | Ph | H | |
| 255 | O | vinyl | Ph | Ph | H | |
| 256 | O | allyl | Ph | Ph | H | |
| 257 | O | acetylenyl | Ph | Ph | H | |
| 258 | O | propargyl | Ph | Ph | H | |
| 259 | O | methoxymethyl | Ph | Ph | H | |
| 260 | O | cyclopropylmethyl | Ph | Ph | H | |
| 261 | O | benzyl | Ph | Ph | H | |
| 262 | O | 4'-methoxybenzyl | Ph | Ph | H | |
| 263 | O | 4'-nitrobenzyl | Ph | Ph | H | |
| 264 | O | 4'-trifluoro-methylbenzyl | Ph | Ph | H | |
| 265 | O | 4'-methylbenzyl | Ph | Ph | H | |
| 266 | O | 2',4'-dichloro-benzyl | Ph | Ph | H | |
| 267 | O | Me | Ph | Ph | H | |
| 268 | O | Ph | 4-n-octyl-phenyl | Ph | H | |
| 269 | O | Me | 4-n-octyl-thiophenyl | Ph | H | |
| 270 | O | Me | 4-(2-octenyl)-phenyl | Ph | H | |
| 271 | O | Me | 4-(2-octenyloxy-phenyl | Ph | H | |
| 272 | O | Me | 4-(2-propenyl)-phenyl | Ph | H | |
| 273 | O | Me | 4-(2-butynyl)-phenyl | Ph | H | |
| 274 | O | H | Me | Ph | H | |
| 275 | O | H | t-Bu | Ph | H | |
| 276 | O | H | i-Pr | Ph | H | |
| 277 | O | H | cyclo-hexyl | Ph | H | |
| 278 | O | Me | Me | Ph | H | 115 |
| 279 | O | benzyl | Me | Ph | H | |
| 280 | O | Me | phenoxy-methyl | Ph | H | |
| 281 | O | Me | n-hexyl | Ph | H | |
| 282 | O | Me | 4-chloro-phenyl | Ph | H | 116 |
| 283 | O | Me | 3-chloro-phenyl | Ph | H | |
| 284 | O | Me | 2-chloro-phenyl | Ph | H | |
| 285 | O | Me | 4-fluoro-phenyl | Ph | H | 102 |
| 286 | O | Me | 3-fluoro- | Ph | H | |

TABLE 1-continued

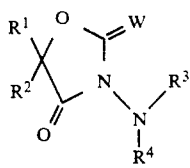

| EX # | W | R¹ | R² | R³ | R⁴ | mp(°C.) |
|---|---|---|---|---|---|---|
| 287 | O | Me | 4-bromophenyl | Ph | H | |
| 288 | O | Me | 3,5-dichlorophenyl | Ph | H | |
| 289 | O | Me | 3,4-dichlorophenyl | Ph | H | |
| 290 | O | Me | 2,4-dichlorophenyl | Ph | H | 152 |
| 291 | O | Me | 2-fluorophenyl | Ph | H | 149 |
| 292 | O | Et | 2-fluorophenyl | Ph | H | |
| 293 | O | H | 2-fluorophenyl | Ph | H | |
| 294 | O | vinyl | 2-fluorophenyl | Ph | H | |
| 295 | O | Me | 2-fluorophenyl | 4-fluorophenyl | | |
| 296 | O | Me | 2-fluorophenyl | 2-methylphenyl | H | 140 |
| 297 | O | Me | 2-fluorophenyl | 4-methylphenyl | H | 138 |
| 298 | O | Me | 2-fluorophenyl | 2,6-dichlorophenyl | H | |
| 299 | O | Me | 2-fluorophenyl | Ph | Me | |
| 300 | O | Me | 2,3-difluorophenyl | Ph | H | |
| 301 | O | Me | 2,5-difluorophenyl | Ph | H | 141 |
| 302 | O | Me | 3,5-difluorophenyl | Ph | H | |
| 303 | O | Me | 2,6-difluorophenyl | Ph | H | |
| 304 | O | Me | 3,4-difluorophenyl | Ph | H | |
| 305 | O | Me | 2,4-difluorophenyl | Ph | H | 142 |
| 306 | O | Et | 2,4-difluorophenyl | Ph | H | |
| 307 | O | H | 2,4-difluorophenyl | Ph | H | |
| 308 | O | vinyl | 2,4-difluorophenyl | Ph | H | |
| 309 | O | Me | 2,4-difluorophenyl | Ph | Me | 129 |
| 310 | O | Me | 2,4-difluorophenyl | 2,6-dichlorophenyl | H | |
| 311 | O | Me | 2,4-difluorophenyl | 4-fluorophenyl | H | |
| 312 | O | Me | 2,4-difluorophenyl | 4-methylphenyl | H | |
| 313 | O | Me | 2,4-dichlorophenyl | 2-methylphenyl | H | |
| 314 | O | Me | 2-methylphenyl | Ph | H | 140 |
| 315 | O | Me | 4-methylphenyl | Ph | H | 128 |
| 316 | O | Me | 2,5-dimethylphenyl | Ph | H | |
| 317 | O | Me | 4-t-butylphenyl | Ph | H | |
| 318 | O | Me | 4-cyclohexylphenyl | Ph | H | |
| 319 | O | Me | 3-trifluoromethylphenyl | Ph | H | |
| 320 | O | Me | 3-nonafluorobutylphenyl | Ph | H | |
| 321 | O | Me | 2-methoxyphenyl | Ph | H | |
| 322 | O | Me | 4-methoxyphenyl | Ph | H | 104 |
| 323 | O | Me | 4-n-pentyloxyphenyl | Ph | H | 128 |
| 324 | O | Me | 4-allyloxyphenyl | Ph | H | |
| 325 | O | Me | 3-methylthiophenyl | Ph | H | |
| 326 | O | Me | 4-trifluoromethylthiophenyl | Ph | H | |
| 327 | O | Me | 4-trifluoromethoxyphenyl | Ph | H | |

TABLE 1-continued

| EX # | W | R¹ | R² | R³ | R⁴ | mp(°C.) |
|---|---|---|---|---|---|---|
| 328 | O | M | 2-cyanophenyl | Ph | H | |
| 329 | O | Me | 4-cyanophenyl | Ph | H | |
| 330 | O | Me | 4-phenoxyphenyl | Ph | H | 142 |
| 331 | O | Et | 4-phenoxyphenyl | Ph | H | |
| 332 | O | H | 4-phenoxyphenyl | Ph | H | |
| 333 | O | Me | 4-phenoxyphenyl | Ph | Me | 95 |
| 334 | O | Me | 4-phenoxyphenyl | 2-methyl-phenyl | H | 118 |
| 335 | O | Me | 4-phenoxyphenyl | 4-methyl-phenyl | H | |
| 336 | O | Me | 4-phenoxyphenyl | 4-fluoro-phenyl | H | |
| 337 | O | Me | 3-phenoxyphenyl | Ph | H | |
| 338 | O | Me | 2-phenoxyphenyl | Ph | H | |
| 339 | O | Me | 4-(4-chlorophenoxy)-phenyl | Ph | H | |
| 340 | O | Me | 4-(4-bromophenoxy)-phenyl | Ph | H | 162 |
| 341 | O | Me | 4-(4-fluorophenoxy)-phenyl | Ph | H | |
| 342 | O | Me | 4-(3-fluorophenoxy)-phenyl | Ph | H | |
| 343 | O | Me | 4-(2-fluorophenoxy)-phenyl | Ph | H | |
| 344 | O | Me | 4-(4-nitrophenoxy)- | Ph | H | 63 |
| 345 | O | Me | 4-(4-methylphenoxy)-phenyl | Ph | H | |
| 346 | O | Me | 4-(2-methylphenoxy)-phenyl | Ph | H | |
| 347 | O | Me | 4-benzyloxyphenyl | Ph | H | |
| 348 | O | Me | 2-fluoro-4-phenoxyphenyl | Ph | H | 129 |
| 349 | O | Me | 4-carbomethoxy-phenyl | Ph | H | |
| 350 | O | Me | 4-carbophenoxy-phenyl | Ph | H | |
| 351 | O | H | 3-(3,5-dichloro-phenoxy)phenyl | Ph | H | |
| 352 | O | H | 3-(3-trifluoro-methylphenoxy)phenyl | Ph | H | |
| 353 | O | H | 3-phenoxyphenyl | Ph | H | |
| 354 | O | Me | 4-(4-trifluoro-methylphenoxy)phenyl | Ph | H | |
| 355 | O | Me | 4-(4-methoxy-phenoxy)phenyl | Ph | H | 153 |
| 356 | O | Me | 4-(2,4-dichloro-phenoxy)phenyl | Ph | H | 125 |
| 357 | O | Me | 4-methanesul-fonylphenyl | Ph | H | |
| 358 | O | Me | 4-nitrophenyl | Ph | H | 116 |
| 359 | O | Me | 3-trifluoro-methylphenyl | Ph | H | |
| 360 | O | Me | 4-phenylthiophenyl | Ph | H | |
| 361 | O | Me | 4-phenylphenyl | Ph | H | |
| 362 | O | Me | 2-naphthyl | Ph | H | |
| 363 | O | Me | 1-naphthyl | Ph | H | |
| 364 | O | Me | 2-thienyl | Ph | H | |
| 365 | O | Me | 5-chloro-2-thienyl | Ph | H | |
| 366 | O | Me | 5-methyl-2-thienyl | Ph | H | |
| 367 | O | Me | 3-methoxy-2-thienyl | Ph | H | |
| 368 | O | Me | 3-thienyl | Ph | H | 146 |
| 369 | O | Me | 2,5-dichloro-3-thienyl | Ph | H | |
| 370 | O | Me | 2,5-dimethyl-3-thienyl | Ph | H | |
| 371 | O | Me | 2-phenoxy-3-thienyl | Ph | H | |
| 372 | O | Me | 2-nitro-4-thienyl | Ph | H | |
| 373 | O | Me | 3-methoxy-4-thienyl | Ph | H | |
| 374 | O | Me | 2-furyl | Ph | H | |
| 375 | O | Me | 3-furyl | Ph | H | |
| 376 | O | Me | 2-pyridyl | Ph | H | |
| 377 | O | Me | 3-pyridyl | Ph | H | |
| 378 | O | Me | 2-fluoro-3-pyridyl | Ph | H | |
| 379 | O | Me | 4-pyridyl | Ph | H | |

TABLE 1-continued

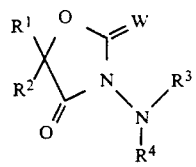

| EX # | W | R¹ | R² | R³ | R⁴ | mp(°C.) |
|---|---|---|---|---|---|---|
| 380 | O | Me | 3-fluoro-4-pyridyl | Ph | H | 131 |
| 381 | O | | —CH₂(CH₂)₃CH₂— | Ph | H | |
| 382 | O | | —CH₂(CH₂)₃CH₂— | 3,5-dichlorophenyl | H | |
| 383 | O | | —CH₂CH₂NMeCH₂CH₂— | Ph | H | |
| 384 | O | | —CH₂CH₂SCH₂CH₂— | Ph | H | |
| 385 | O | | indanyl | Ph | H | |
| 386 | O | | tetrahydronaphthyl | Ph | H | |
| 387 | O | Me | 4-fluoro-3-pyridyl | Ph | H | |
| 388 | O | Me | 3-fluoro-2-pyridyl | Ph | H | |
| 389 | O | | butylthienyl | | | |
| 390 | O | Me | 4-carbomethoxyphenyl | Ph | H | |
| 391 | O | Me | 4-benzylphenyl | Ph | H | |
| 392 | O | | biphenyl | Ph | H | |
| 393 | O | Me | Ph | 3,5-dichlorophenyl | H | |
| 394 | O | cyclopropyl | Ph | 3,5-dichlorophenyl | H | |
| 395 | O | Me | phenoxymethyl | 3,5-dichlorophenyl | H | |
| 396 | O | Me | Ph | 2,6-dichlorophenyl | H | |
| 397 | O | Me | 4-phenoxyphenyl | 2,6-dichlorophenyl | H | |
| 398 | O | Me | phenoxymethyl | 2,6-dichlorophenyl | H | |
| 399 | O | H | t-Bu | 2,6-dichlorophenyl | H | |
| 400 | O | Me | Ph | 4-fluorophenyl | H | |
| 401 | O | Me | 4-fluorophenyl | 4-fluorophenyl | H | |
| 402 | O | Me | 4-cyclohexylphenyl | 4-fluorophenyl | H | |
| 403 | O | Me | phenylthiomethyl | 4-fluorophenyl | H | |
| 404 | O | Me | Ph | 3-fluorophenyl | H | 164 |
| 405 | O | Me | Ph | 4-chlorophenyl | H | |
| 406 | O | Me | Ph | 3-chlorophenyl | H | 59 |
| 407 | O | Me | 4-methoxyphenyl | 3-chlorophenyl | H | 152 |
| 408 | O | Me | Ph | 2-fluorophenyl | H | |
| 409 | O | Me | Ph | 2,5-difluorophenyl | H | |
| 410 | O | Me | Ph | 4-methylphenyl | H | |
| 411 | O | Me | 4-fluorophenyl | 4-methylphenyl | H | |
| 412 | O | Me | 4-phenoxyphenyl | 4-methylphenyl | | |
| 413 | O | Me | phenylthiomethyl | 4-methylphenyl | H | |
| 414 | O | Me | phenoxymethyl | 4-methylphenyl | H | |
| 415 | O | Me | Ph | 2,6-dimethylphenyl | H | |

TABLE 1-continued

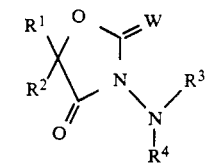

| EX # | W | R¹ | R² | R³ | R⁴ | mp(°C.) |
|---|---|---|---|---|---|---|
| 416 | O | Me | Ph | 4-t-butylphenyl | H | |
| 417 | O | Me | Ph | 3-methylphenyl | H | |
| 418 | O | Me | Ph | 2-methylphenyl | H | |
| 419 | O | Me | Ph | 4-methoxyphenyl | H | 134 |
| 420 | O | Me | Ph | 4-n-pentyloxyphenyl | H | |
| 421 | O | Me | Ph | 4-allyloxyphenyl | H | |
| 422 | O | Me | Ph | 4-trifluoromethylphenyl | H | |
| 423 | O | Me | Ph | 3-trifluoromethylphenyl | H | |
| 424 | O | Me | Ph | 2-trifluoromethylphenyl | H | 141 |
| 425 | O | Me | Ph | 4-nitrophenyl | H | |
| 426 | O | Me | Ph | 4-cyanophenyl | H | |
| 427 | O | Me | Ph | 4-carbomethoxyphenyl | H | |
| 428 | O | Me | Ph | benzyl | H | |
| 429 | O | Me | Ph | 2-thienyl | H | |
| 430 | O | Me | Ph | 3-furyl | H | |
| 431 | O | Me | Ph | 2-pyridyl | H | |
| 432 | O | Me | Ph | 5-trifluoromethyl-2-pyridyl | H | |
| 433 | O | Me | Ph | 2-pyrimidyl | H | |
| 434 | O | Me | Ph | 6-chloro-3-pyridazyl | H | |
| 435 | O | Me | Ph | ethyl | H | |
| 436 | O | Me | Ph | cyclohexyl | H | |
| 437 | O | Me | Ph | t-Bu | H | |
| 438 | O | Me | Ph | n-decyl | H | |
| 439 | O | Me | Ph | Ph | formyl | |
| 440 | O | Me | Ph | Ph | acetyl | |
| 441 | O | Me | Ph | Ph | trifluoroacetyl | |
| 442 | O | Me | Ph | Ph | methoxyacetyl | |
| 443 | O | Me | Ph | Ph | methoxycarbonyl | |
| 444 | O | Me | Ph | Ph | methylaminocarbonyl | |
| 445 | O | Me | Ph | Ph | methanesulfonyl | |
| 446 | O | Me | 3-thienyl | Ph | methyl | 118 |
| 447 | O | 4-fluorophenyl | Ph | Ph | methyl | |
| 448 | O | Me | Ph | Ph | methyl | 131 |
| 449 | O | Me | Ph | Ph | phenylaminocarbonyl | |
| 450 | O | Me | Ph | Ph | allyl | |
| 451 | O | Me | Ph | Ph | propargyl | |
| 452 | O | Me | Ph | Ph | cyclobutyl | |
| 453 | O | Me | Ph | Ph | benzyl | |
| 454 | O | Me | Ph | 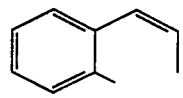 | | |
| 455 | O | Me | 2-cyanophenyl | 2-methylphenyl | H | |
| 456 | O | Me | 2-N,N-dimethylaminophenyl | Ph | H | |
| 457 | O | Me | 3-pyridyl | Ph | H | |
| 458 | O | Ph | 4-pyridyl | Ph | H | |
| 459 | S | vinyl | phenyl | 4-fluorophenyl | H | 64 |
| 460 | S | Me | 4-(6,6,6-trichlorohexylthio)phenyl | Ph | H | |
| 461 | S | Me | 4-(6,6,6-trifluorohexyloxy)phenyl | Ph | H | |
| 462 | S | Me | 4-(trifluoromethanesulfonyl)phenyl | Ph | H | |
| 463 | S | Me | 4-(2'-fluorobenzyloxy)phenyl | Ph | H | |
| 464 | S | Me | 4-(4'-phenoxybenzyloxy)- | Ph | H | |

TABLE 1-continued

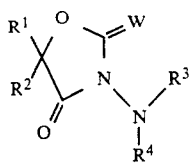

| EX # | W | R¹ | R² | R³ | R⁴ | mp(°C.) |
|---|---|---|---|---|---|---|
| 465 | S | Me | 3-fluoro-4-phenoxyphenyl | Ph | H | |
| 466 | O | Me | 3-fluoro-4-phenoxyphenyl | Ph | H | |
| 467 | S | Me | 2-fluoro-4-(2-fluorophenoxy)-phenyl | Ph | H | |
| 468 | O | Me | 2-fluoro-4-(2-fluorophenoxy)-phenyl | Ph | H | |
| 469 | S | Me | 4-(2,4-di-fluoro-phenoxy)phenyl | Ph | H | |
| 470 | O | Me | 4-(2,4-di-fluoro-phenoxy)phenyl | Ph | H | |
| 471 | S | Me | 4-(4-n-butyloxy-phenoxy)phenyl | Ph | H | |
| 472 | S | Me | 4-(4-n-butyl-phenoxy)phenyl | Ph | H | |
| 473 | S | Me | 4-(4-cyclo-hexyloxy-phenoxy)phenyl | Ph | H | |
| 474 | S | Me | 4-(4-methoxy-methyl)phenyl | Ph | H | |
| 475 | S | Me | 4-phenethyloxy-phenyl | Ph | H | |
| 476 | S | Me | 4-(2'-fluoro-phenyl | Ph | H | |
| 477 | S | Me | Ph | 4-fluoro-2-methyl-phenyl | H | |
| 478 | S | Me | 4-(N-phenyl-amino)phenyl | Ph | H | |
| 479 | S | Me | 4-(N-methyl-amino)phenyl | Ph | H | |
| 480 | O | Me | 4-(N-methyl-amino)phenyl | Ph | H | |
| 481 | S | Me | 4-(N-butyl-amino)phenyl | Ph | H | |
| 482 | S | Me | 4-(N-(2-fluoro-phenyl)amino)-phenyl | Ph | H | |
| 483 | S | Me | 4-(N-(4-methyl-phenyl)amino)-phenyl | Ph | H | |

¹racemic mixture
²(R)-enantiomer
³(S)-enantiomer
⁴racemic mixture
⁵(S)-enantiomer

TABLE 2

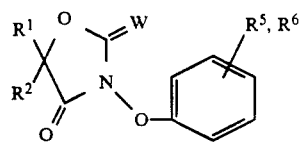

| EX # | W | R¹ | R² | R⁵ | R⁶ | mp (°C.) |
|---|---|---|---|---|---|---|
| 484 | S | Me | Ph | H | H | |
| 485 | O | Me | Ph | H | H | |
| 486 | S | H | Ph | H | H | |
| 487 | S | tri-fluoro-methyl | Ph | H | H | |

TABLE 2-continued

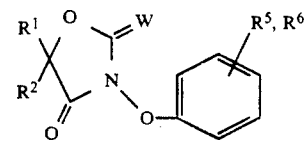

| EX # | W | R¹ | R² | R⁵ | R⁶ | mp (°C.) |
|---|---|---|---|---|---|---|
| 488 | S | Me | 3-thienyl | H | H | |
| 489 | S | Me | 4-fluorophenyl | H | H | |
| 490 | S | Me | 2,4-difluoro-phenyl | H | H | 82 |
| 491 | S | Me | 4-phenoxy-phenyl | H | H | oil |

TABLE 2-continued

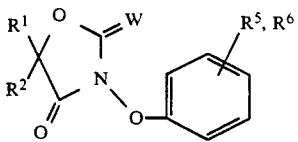

| EX # | W | R$^1$ | R$^2$ | R$^5$ | R$^6$ | mp (°C.) |
|---|---|---|---|---|---|---|
| 492 | S | Me | 3-trifluoro-methylphenyl | H | H | |
| 493 | S | Me | Ph | 4-fluoro | H | |
| 494 | S | Me | Ph | 3-trifluoro-methyl | H | |
| 495 | S | Me | Ph | 4-phenoxy | H | |
| 496 | S | Me | Ph | 2-chloro | 4-chloro | |
| 497 | S | Me | Ph | 2-Me | 6-Me | |

Formulation

The compounds of this invention will generally be used in formulation with a liquid or solid diluent or with an organic solvent. Useful formulations of the compounds of Formula I can be prepared in conventional ways. They include dusts, granules, pellets, solutions, emulsions, wettable powders, emulsifiable concentrates and the like. Many of these may be applied directly. Sprayable formulations can be extended in suitable media and used at spray volumes of from about one to several hundred liters per hectare. High strength compositions are primarily used as intermediates for further formulation. The formulations, broadly, contain about 1% to 99% by weight of active ingredient(s) and at least one of a) about 0.1% to 35% surfactant(s) and b) about 5% to 99% solid or liquid inert diluent(s). More specifically, they will contain these ingredients in the following approximate proportions:

| | Active Ingredient | Percent by Weight Diluent(s) | Surfactant(s) |
|---|---|---|---|
| Wettable Powders | 20-90 | 0-74 | 1-10 |
| Oil Suspensions, Emulsions, Solutions, (including Emulsifiable Concentrates) | 5-50 | 40-95 | 0-35 |
| Aqueous Suspensions | 10-50 | 40-84 | 1-20 |
| Dusts | 1-25 | 70-99 | 0-5 |
| Granules and Pellets | 1-95 | 5-99 | 0-15 |
| High Strength Compositions | 90-99 | 0-10 | 0-2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Welkins, et al., "Handbook of Insecticide Dust Diluents and Carriers", 2nd Ed., Dorland Books, Caldwell, New Jersey. The more absorptive diluents are preferred for the wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspension are prepared by wet milling (see, for example, Littler, U.S. Pat. No. 3,060,804). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 4th Edn., McGraw-Hill, N.Y., 1963, pp. 8-59ff.

For further information regarding the art of formulation, see for example:

H. M. Loux, U.S. Pat. No. 3,235,361, Feb. 15, 1966, Col. 6, Line 16 through Col. 7, Line 19 and Examples 10 through 41.

R. W. Luckenbaugh, U.S. Pat. No. 3,309,192, Mar. 14, 1967, Col. 5, Line 43 through Col. 7, Line 62 and Examples 8, 12, 15, 39, 41, 52, 53, 58, 132, 138-140, 162-164, 166, 167, 169-182.

H. Gysin and E. Knusli, U.S. Pat. No. 2,891,855, Jun. 23, 1959, Col. 3, Line 66 through Col. 5, Line 17 and Examples 1-4.

G. C. Klingman, "Weed Control as a Science", John Wiley and Sons, Inc., New York, 1961, pp. 81-96.

J. D. Fryer and S. A. Evans, "Weed Control Handbook", 5th Edn. Blackwell Scientific Publications, Oxford, 1968, pp. 101-103.

Examples of useful formulations of compounds of the present invention are as follows.

EXAMPLES

Examples 217

| Wettable Power | |
|---|---|
| 5-methyl-5-phenyl-3-(phenylamino)-2-thioxo-4-oxazolidinone | 80% |
| Sodium Alkylnaphthalenesulfonate | 4% |
| Sodium Ligninsulfonate | 2% |
| Synthetic Amorphous Silica | 1% |
| Kaolinite | 13% |

The ingredients are blended, hammermilled, re-blended and packaged.

EXAMPLE 218

| High Strength Concentrate | |
|---|---|
| 5-methyl-5-phenyl-3-(phenylamino)-2-thioxo-4-oxazolidinone | 98.5% |
| Silica Aerogel | 0.5% |
| Synthetic Amorphous Silica | 1.0% |

The ingredients are blended and ground in a hammermill to produce a high strength concentrate essentially all passing a U.S.S. No. 50 Sieve (0.3 mm openings). This material may then be formulated in a variety of ways.

EXAMPLE 219

Solution

| Solution | |
| --- | --- |
| 5-methyl-5-phenyl-3-(phenylamino)-2-thioxo-4-oxazolidinone | 25% |
| N-methyl-2-pyrrolidone | 75% |

The ingredients are combined and stirred to produce a solution, which can be used for low volume applications.

EXAMPLE 220

| Emulsifiable Concentrate | |
| --- | --- |
| 5-methyl-5-phenyl-3-(phenylamino)-2-thioxo-4-oxazolidinone | 15% |
| Blend of calcium sulfonates and non-ionic surfactants | 6% |
| Acetophenone | 79% |

The ingredients are combined and stirred until the active is dissolved. A fine screen filter is included in packaging operation to insure the absence of any extraneous undissolved material in the product.

Utility

The compounds of this invention are useful as plant disease control agents. They provide control of diseases caused by a broad spectrum of plant pathogens in the basidiomycete, and ascomycete classes and particularly against fungi in the oomycete class. They are effective in controlling a broad spectrum of plant diseases, particularly foliar pathogens of ornamental, vegetable, field, cereal and fruit crops, such as *Plasmopara viticola, Phytophthora infestans, Peronospora, tabacina, Pseudoperonospora cubensis, Phytophthora megasperma, Botrytis cinerea, Venturia inaequalis, Puccinia recondita, Pythium aphanidermatum, Alternaria brassicola, Septoria nodorum, Cercosporidium personatum* and species related to these pathogens.

The compounds of this invention can be mixed with fungicides, bactericides, acaricides, nematicides, insecticides or other biologically active compounds in order to achieve desired results with a minimum of expenditure of time, effort and material. Suitable agents of this type are well-known to those skilled in the art. Some are listed below:

Fungicides methyl 2-benzimidazolecarbamate (carbendazim)
tetramethylthiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
2-cyano-N-ethylcarbamoyl-2-methoxyiminoacetamide (cymoxanil)
N-trichloromethylthiotetrahydrophthalamide (captan)
N-trichloromethylthiophthalimide (folpet)
dimethyl 4,4'-(o-phenylene)bis(3-trioallophanate) (thiophanate-methyl)
2-(thiazol-4-yl)benzimidazole (thiabendazole)
aluminum tri(O-ethyl phosphonate)(phosethyl aluminum)
tetrachloroisophthalonitrile (chlorothalonil)
2,6-dichloro-4-nitroaniline (dichloran)
N-(2,6-dimethylphenyl)-N-(methoxyacetyl)alanine methyl ester (metalaxyl)
cis-N-[1,1,2,2-tetrachloroethyl)thio]cyclohex-4-ene-1,2-dicarbioximide (captafol)
3-(3,5-dichlorophenyl)-N-(1-methylethyl)-2,4-dioxo-1-imidazolidine carboxamide (iprodione)
3-(3,5-dichlorophenyl)-5-ethenyl-5-methyl-2,4-oxazolidinedione (vinclozolin)
kasugamycin
O-ethyl-S,S-diphenylphosphorodithioate (edifenphos)
4-(3-(4-(1,1-dimethylethyl)phenyl)-2-methyl)propyl-2,6-dimethylmorpholine (fenpropiomorph)
4-(3-4-(1,1-dimethylethyl)phenyl)-2-methyl)propyl-piperidine (fenpropidine)
1-(4-chlorophenoxy)-3,3-dimethyl-1-(1H-1,2,4-triazol-1-yl)butane (triadimefon)
2-(4-chlorophenyl)-2-(1H-1,2,4-triazol-1-ylmethyl)hexanenitrile (mycolobutanil)
tebuconazol
3-chloro-4-[4-methyl-2-(1H-1,2,4-triazol)-1-ylmethyl)-1,3-dioxolan-2-yl]phenyl-4-chlorophenylether (difenaconazole)
1-[2-(2,4-dichlorophenyl)pentyl]1H-1,2,4-triazole (penconazole)
α-(2-fluorophenyl)-α-(4-fluorophenyl)-1H-1,2,4-triazole-1-ethanol (flutriafol)
2-methoxy-N-(2-oxo-1,3-oxazolidin-3-yl)acet-2,6-xylidide (oxadixyl)
1-[[bis(4-fluorophenyl)methylsilyl]methyl]-1H-1,2,4-triazole (flusilazole)
1-N-propyl-N-[2(2,4,6-trichlorophenoxyl)ethyl]carbamoylimidazole (prochloraz)
1-[[2-(2,4-dichlorophenyl)-4-propyl-1,3-dioxolan-2-yl]methyl]-1H-1,2,4-triazole (propiconazole)
α-(2-chlorophenyl)-α-(4-chlorophenyl)-5-pyridinemethanol (fenarimol)
copper oxychloride
methyl N-(2,6-dimethyl-phenyl)-N-(2-furanylcarbonyl)-DL-alaninate (furalazyl)
hexaconazole
4-chloro-N-(cyanoethyoxymethyl)benzamide
4-[3-(4-chlorophenyl)-3-(3,4-dimethoxyphenyl)-1-oxo-2-propenyl]morpholine

Bactericides tribasic copper sulfate
streptomycin sulfate
oxytetracycline

Acaricides senecioic acid, ester with 2-sec-butyl-4,6-dinitrophenol (binapacryl)
6-methyl-1,3-dithiolo[2,3-B]quinonolin-2-one (oxythioquinox)
2,2,2-trichloro-1,1-bis(4-chlorophenyl)ethanol (dicofol)
bis(pentachloro-2,4-cyclopentadien-1-yl) (dietnochlor)
tricylcohexyltin hydroxide (cyhexatin)
hexakis(2-methyl-2-phenylpropyl)distannoxane (fenbutin oxide)

Nematicides

2-[diethoxyphosphinylimino]-1,3-diethietane (fosthietan)
S-methyl-1-(dimethylcarbamoyl)-N-(methylcarbamoyloxy)thioformimidate (oxamyl)

S-methyl-1-carbamoyl-N-(methylcarbamoyloxy)thioformimidate

N-isopropylphosphoramidic acid, O-ethyl-O'-[4-(methylthio)-m-tolyl]diester (fenamiphos)

Insecticides 3-hydroxy-N-methylcrotonamide(dimethylphosphate)ester (monocrotophos)

methylcarbamic acid, ester with 2,3-dihydro-2,2-dimethyl-7-benzofuranol (carbofuran)

O-[2,4,5-trichloro-α-(chloromethyl)benzyl]phosphoric acid O', O'-dimethyl ester (tetrachlorovinphos)

2-mercaptosuccinic acid, diethyl ester, S-ester with thionophosphoric acid, dimethyl ester (malathion)

phosphorothioic acid, O,O-dimethyl, O-p-nitrophenyl ester (methyl parathion)

methylcarbamic acid, ester with α-naphthol (carbaryl)

methyl N-[[(methylamino)carbonyl]oxy]ethanimidothioate (methomyl)

N'-(4-chloro-o-tolyl)-N,N-dimethylformamidine (chlorodimeform)

O,O-diethyl-O-(2-isopropyl-4-methyl-6-pyrimidyl)-phosphorothioate (diazinon)

octachlorocamphene (toxaphene)

O-ethyl O-p-nitrophenyl phenylphosphonothioate (EPN)

cyano(3-phenoxyphenyl)-methyl 4-chloro-α-(1-methylethyl)benzene acetate (fenvalerate)

(3-phenoxyphenyl)methyl (±)-cis,trans-3-(2,2-dichloroethenyl)-2,2-dimethylcyclopropanecarboxylate (permethrin)

dimethyl, N,N'-[thiobis(N-methylimmo)carbonyloxyl]-bis[ethanimidothioate) (thiodicarb)

phosphorothiolothionic acid, O-ethyl-O-[4-(methylthio)phenyl]-S-n-propyl ester (sulprofos)

α-cyano-3-phenoxybenzyl 3-(2,2-dichlorovinyl)-2,2-dimethylcyclopropane carboxylate (cypermethrin)

cyano(3-phenoxyphenyl)methyl 4-(difluoromethoxy)-α-(methylethyl)benzene acetate (flucythrinate)

O,O-diethyl-O-(3,5,6-trichloro-2-pyridyl)phosphorothioate (chlorpyrifos)

O,O-dimethyl-S-[(4-oxo-1,2,3-benzotriazin-3-(4H)-yl)methyl]phosphorodithioate (azinphos-methyl)

5,6-dimethyl-2-dimethylamino-4-pyrimidinyl diemthyl carbamate (pirimicarb)

S-(N-formyl-N-methylcarbamoylmethyl)-O,O-dimethyl phosphorodithioate (formothion)

S-2-(ethylthioethyl)-O,O-dimethyl phosphiorothioate (demeton-S-methyl)

α-cyano-3-phenoxybenzyl cis-3(2,2-dibromovinyl)-2,2-dimethylcyclopropane carboxylate (deltamethrin)

cyano(3-phenoxyphenyl)methyl ester of N-(2-chloro-4-trifluoromethylphenyl)alanine (fluvalinate)

In some instances, combinations with other fungicides having a similar spectrum of disease control but a different mode of action will be particularly advantageous for resistance management and/or improved properties such as curative activity for established infections. A particularly effective combination in both regards is one involving a compound of Formula I and cynoxanil.

Application

Disease control is ordinarily accomplished by applying an effective amount of the compound either pre- or post-infection to the portion of the plant to be protected such as the roots, stems, foliage, fruit, seeds, tubers or bulbs. The compound may also be applied to the seen from which the plants to be protected are to be grown.

Rates of application for these compounds can be influenced by many factors of the environment and should be determined under actual use conditions. Foliage can normally be protected when treated at a rate of from less than 1 g/ha to 10,000 g/ha of active ingredient. Seed and seedlings can normally be protected when seed is treated at a rate of from 0.1 to 10 grams per kilogram of seed.

EXAMPLE A

The test compounds were dissolved in acetone is an amount equal to 3% of the final volume and then suspended at a concentration of 200 ppm in purified water containing 250 ppm of the surfactant Trem 014 (polyhydric alcohol esters). This suspension was sprayed to the point of run-off on apple seedlings. The following day the seedlings were inoculated with a spore suspension of *Venturia inaequalis* (the causal agent of apple scab) and incubated in a saturated atmosphere at 20° C. for 24 hr., and then moved to a growth chamber at 22° C. for 11 days, after which disease ratings were made.

EXAMPLE B

The test compounds were dissolved in acetone in an amount equal to 3% of the final volume and then suspended at a concentration of 200 ppm in purified water containing 250 ppm of the surfactant Trem 014 (polyhydric alcohol esters). This suspension was sprayed to the point of run-off on peanut seedlings. The following day the seedlings were inoculated with a spore suspension of *Cercosporidium personatum* (the causal agent of peanut late leafspot) and incubated in a saturated atmosphere at 22° C. for 24 hr, a high humidity atmosphere at 22° to 30° C. for 5 days, and then moved to a growth chamber at 29° C. for 6 days after which disease ratings were made.

EXAMPLE C

The test compounds were dissolved in acetone in an amount equal to 3% of the final volume and then suspended at a concentration of 200 ppm in purified water containing 250 ppm of the surfactant Trem 014 (polyhydric alcohol esters). This suspension was sprayed to the point of run-off on wheat seedlings. The following day the seedlings were inoculated with a spore suspension of *Puccinia recondita* (the causal agent of wheat leaf rust) and incubated in a saturated atmosphere at 20° C. for 24 hr, and then moved to a growth chamber at 20° C. for 6 days, after which disease ratings were made.

EXAMPLE D

The test compounds were dissolved in acetone in an amount equal to 3% of the final volume and then suspended at a concentration of 200 ppm in purified water containing 250 ppm of the surfactant Trem 014 (polyhydric alcohol esters). This suspension was sprayed to the point of run-off on tomato seedlings. The following day the seedlings were inoculated with a spore suspension of *Phytophthora infestans* (the causal agent of potato and tomato late blight) and incubated in a saturated atmosphere at 20° C. for 24 hr, and then moved to a growth chamber at 20° C. for 5 days, after which disease ratings were made.

EXAMPLE E

The test compounds were dissolved in acetone in an amount equal to 3% of the final volume and then suspended at a concentration of 40 ppm in purified water containing 250 ppm of the surfactant Trem 014 (polyhydric alcohol esters). The suspension was sprayed to the point of run-off on grape seedlings. The following day the seedlings were inoculated with a spore suspension of *Plasmopara viticola* (the causal agent of grape downy mildew) and incubated in a saturated atmosphere at 20° C. for 24 hours, moved to a growth chamber at 20° C. for 6 days, and then incubated in a saturated atmosphere at 20° C. for 24 hours, after which the disease ratings were made.

EXAMPLE F

The test compounds were dissolved in acetone in an amount equal to 3% of the final volume and then suspended at a concentration of 200 ppm in purified water containing 250 ppm of the surfactant Trem 014 (polyhydric alcohol esters). This suspension was sprayed to the point of run-off on cucumber seedlings. The following day the seedlings were inoculated with a spore suspension of *Botrytis cinerea* (the causal agent of gray mold on many crops) and incubated in a saturated atmosphere at 20° C. for 48 hr, and moved to a growth chamber at 20° C. for 5 days, after which disease ratings were made.

EXAMPLE G

The test compounds were dissolved in acetone in an amount equal to 3% of the final volume and then suspended at a concentration of 40 ppm in purified water containing 250 ppm of the surfactant Trem 014 (polyhydric alcohol esters). The suspension was sprayed to the point of run-off on tobacco seedlings. The following day the seedlings were inoculated with a spore suspension of *Peronospora tabacina* (the causal agent of tobacco blue mold) and incubated in a saturated atmosphere at 20° C. for 24 hours, moved to a growth chamber at 22° C. for 6 days, and then incubated in a saturated atmosphere at 20° C. for 24 hours, after which the disease ratings were made.

EXAMPLE H

The test compounds were dissolved in acetone in an amount equal to 3% of the final volume and then suspended at a concentration of 40 ppm in purified water containing 250 ppm of the surfactant Trem 014 (polyhydric alcohol esters). The suspension was sprayed to the point of run-off on cucumber seedlings. The following day the seedlings were inoculated with a spore suspension of *Pseudoperonospora cubensis* (the causal agent of cucumber downy mildew) and incubated in a saturated atmosphere at 20° C. for 24 hours, moved to a growth chamber at 20° C. for 6 days, and the incubated in a saturated atmosphere at 20° C. for 24 hours, after which the disease ratings were made.

EXAMPLE I

The test compounds were dissolved in acetone in an amount equal to 3% of the final volume and then suspended at a concentration of 200 ppm in purified water containing 250 ppm of the surfactant Trem 014 (polyhydric alcohol esters). The suspension was sprayed to the point of run-off on wheat seedlings. The following day the seedlings were inoculated with spores of *Erysiphe graminis* (the causal agent of wheat powdery mildew) and incubated in a growth chamber at 20° C. for 7 days after which disease ratings were made.

EXAMPLE J

The test compounds were dissolved in acetone in an amount equal to 3% of the final volume and then suspended at a concentration of 200 ppm in purified water containing 250 ppm of the surfactant Trem 014 (polyhydric alcohol esters). The suspension was sprayed to the point of run-off on rice seedlings. The following day the seedlings were inoculated with a spore suspension of *Rhizoctoia solani* (the causal agent of rice sheath blight) and incubated in a saturated atmosphere at 27° C. for 48 hours, moved to a growth chamber at 29° C. for 48 hours after which the disease ratings were made.

EXAMPLE K

The test compounds were dissolved in acetone in an amount equal to 3% of the final volume and then suspended at a concentration of 200 ppm in purified water containing 250 ppm of the surfactant Trem 014 (polyhydric alcohol esters). The suspension was sprayed to the point of run-off on rice seedlings. The following day the seedlings were inoculated with a spore suspension of *Pyricularia oryzae* (the causal agent of the rice blast) and incubated in a saturated atmosphere at 27° C. for 24 hours, moved to a growth chamber at 30° C. for 4 days after which the disease ratings were made.

Examples which further illustrate the invention can be found in the following table. In the table, a rating of 100 indicates 100% disease control and a rating of 0 indicates no disease control (relative to the carrier sprayed controls). A "—" indicates that no test was performed at the indicated concentration on that disease.

| CMPD NO. | EX. A | EX. B | EX. C | EX. D | EX. E | EX. F | EX. G | EX. H | EX. I | EX. J | EX. K |
|---|---|---|---|---|---|---|---|---|---|---|---|
| 278 | 36 | 0 | — | 0 | — | 45 | — | — | 0 | 0 | 0 |
| 169 | 64 | 71 | — | 64 | 100 | 0 | 70 | 46 | 0 | 0 | 0 |
| 156 | 39 | 43 | — | 77 | 100 | 96 | — | — | 0 | 0 | 0 |
| 212 | 50 | 0 | — | 0 | 22 | 0 | — | — | 0 | 0 | 0 |
| 3 | 97 | 100 | 100 | 99 | 100 | 0 | 100 | 100 | 0 | 73 | 0 |
| 2 | 92 | 60 | — | 0 | 54 | 5 | 0 | 11 | 0 | 0 | 0 |
| 76 | 0 | 0 | — | 92 | 100 | 0 | — | — | 0 | 0 | 0 |
| 75 | 69 | 18 | — | 21 | 99 | 7 | — | — | 0 | 0 | 23 |
| 208 | 81 | 34 | — | 76 | 72 | 0 | — | — | 0 | 0 | 0 |
| 207 | 4 | 34 | — | 0 | 35 | 0 | — | — | 0 | 0 | 0 |
| 206 | 51 | 33 | — | 25 | 68 | 0 | — | — | 0 | 0 | 0 |
| 13 | 93 | 64 | — | 93 | 54 | 0 | — | — | 0 | 0 | 0 |
| 131 | 30 | 11 | — | 0 | 14 | 0 | — | — | 0 | 0 | 0 |
| 186 | 60 | 60 | — | 0 | 65 | 0 | — | — | 63 | 0 | 0 |
| 193 | 23 | 64 | — | 0 | 29 | 0 | — | — | 0 | 0 | 0 |

-continued

| CMPD NO. | EX. A | EX. B | EX. C | EX. D | EX. E | EX. F | EX. G | EX. H | EX. I | EX. J | EX. K |
|---|---|---|---|---|---|---|---|---|---|---|---|
| 161 | 60 | 26 | — | 0 | 86 | 69 | — | — | 39 | 0 | 0 |
| 42 | 61 | 79 | — | 93 | 97 | 0 | 92 | 79 | 60 | 0 | 0 |
| 282 | 39 | 23 | — | 0 | 88 | 0 | 62 | 67 | 0 | 0 | 0 |
| 45 | 88 | 23 | — | 99 | 100 | 0 | 100 | 100 | 34 | 0 | 22 |
| 285 | 11 | 23 | — | 93 | 99 | 0 | 99 | 100 | 60 | 0 | 0 |
| 83 | 61 | 58 | — | 64 | 100 | 0 | 55 | 62 | 0 | 0 | 0 |
| 322 | 11 | 23 | — | 86 | 75 | 0 | 0 | — | 34 | 0 | 0 |
| 128 | 61 | 23 | — | 64 | 25 | 0 | 0 | — | 34 | 0 | 0 |
| 358 | 39 | 23 | — | 0 | 32 | 0 | 0 | — | 0 | 0 | 0 |
| 1 | 59 | 91 | 100 | 99 | 100 | — | 100 | — | 0 | 0 | 0 |
| 37 | 77 | 23 | — | 0 | 17 | 0 | 0 | — | 34 | 0 | 0 |
| 175 | 39 | 23 | — | 86 | 97 | 0 | 36 | — | 0 | 0 | 0 |
| 406 | 61 | 23 | — | 0 | — | 0 | 46 | — | 34 | 0 | 0 |
| 38 | 39 | 0 | — | 0 | 49 | 0 | 0 | — | 0 | 0 | 0 |
| 96 | 61 | 23 | — | 26 | 100 | 0 | 100 | 100 | 0 | 0 | 22 |
| 407 | 61 | 0 | — | 0 | 34 | 0 | 0 | — | 0 | 0 | 22 |
| 246 | 39 | 23 | — | 47 | 98 | 0 | 91 | 100 | 0 | 0 | 0 |
| 139 | 0 | 43 | — | 99 | 100 | 88 | 92 | 89 | 0 | 0 | 0 |
| 152 | 6 | 0 | — | 47 | 48 | 35 | 0 | 0 | 39 | 0 | 0 |
| 153 | 0 | 0 | — | 0 | 15 | 0 | 0 | 0 | 0 | 0 | 0 |
| 35 | 0 | 0 | — | 0 | 23 | 96 | 0 | 0 | 0 | 0 | 0 |
| 34 | 64 | 0 | — | 0 | — | 88 | 0 | 11 | 39 | 0 | 0 |
| 4 | 39 | 0 | — | 47 | 97 | 99 | 0 | 25 | 0 | 0 | 0 |
| 36 | 81 | 0 | — | 26 | 15 | 79 | 0 | 6 | 0 | 0 | 0 |
| 216 | 39 | 94 | — | 26 | 45 | 35 | 13 | 11 | 39 | 0 | 0 |
| 19 | 39 | 0 | — | 0 | 79 | 63 | 0 | 39 | 0 | 0 | 0 |
| 224 | 6 | 43 | — | 77 | 82 | 0 | 32 | 46 | 39 | 0 | 27 |
| 162 | 39 | 43 | — | 0 | 89 | 0 | 0 | 11 | 0 | 0 | 0 |
| 5 | 81 | 0 | — | 0 | — | 0 | 0 | 0 | 0 | 0 | 0 |
| 10 | 6 | 43 | — | 0 | 77 | 0 | 0 | 0 | 0 | 0 | 0 |
| 163 | 39 | 0 | — | 0 | 58 | 35 | 0 | 6 | 0 | 0 | 0 |
| 171 | — | — | — | — | 36 | — | 0 | 4 | — | — | — |
| 14 | — | — | — | — | 34 | — | 0 | 22 | — | — | — |
| 39 | — | — | — | — | 53 | — | 0 | 11 | — | — | — |
| 191 | 11 | 23 | — | 0 | 73 | 0 | 0 | — | 0 | 0 | 0 |
| 322 | 61 | 23 | — | 0 | 0 | 0 | 0 | — | 0 | 0 | 0 |
| 218 | — | — | — | — | 100 | — | 66 | 11 | — | — | — |
| 79 | — | — | — | — | 13 | — | 0 | 58 | — | — | — |
| 184 | — | — | — | — | 13 | — | 4 | 4 | — | — | — |
| 164 | — | — | — | — | 62 | — | 0 | 7 | — | — | — |
| 167 | — | — | — | — | 3 | — | 9 | 4 | — | — | — |
| 172 | — | — | — | — | 58 | — | 0 | 38 | — | — | — |
| 183 | — | — | — | — | 58 | — | 0 | 7 | — | — | — |
| 33 | — | — | — | — | 4 | — | 0 | 7 | — | — | — |
| 169 | — | — | — | — | 100 | — | 47 | 36 | — | — | — |
| 168 | — | — | — | — | 59 | — | 0 | 29 | — | — | — |
| 180 | — | — | — | — | 100 | — | 0 | 49 | — | — | — |
| 165 | — | — | — | — | 15 | — | 0 | 11 | — | — | — |
| 181 | — | — | — | — | 100 | — | 77 | 22 | — | — | — |
| 170 | — | — | — | — | 100 | — | 17 | 49 | — | — | — |
| 182 | — | — | — | — | 15 | — | 21 | 22 | — | — | — |
| 166 | — | — | — | — | 2 | — | 0 | 40 | — | — | — |
| 54 | 46 | 21 | — | 86 | 89 | 0 | — | — | 0 | 0 | 0 |
| 65 | 46 | 98 | — | 100 | 100 | 0 | 100 | 100 | 0 | 0 | 0 |
| 70 | 0 | 21 | — | 0 | 0 | 0 | — | — | 0 | 0 | 0 |
| 80 | 0 | 11 | — | 0 | 3 | 6 | — | — | 0 | 0 | 0 |
| 209 | 0 | 0 | — | 0 | 12 | 6 | — | — | 0 | 0 | 0 |
| 132 | 30 | 11 | — | 0 | 43 | 90 | — | — | 0 | 0 | 0 |
| 78 | 0 | 11 | — | 0 | 25 | 6 | — | — | 0 | 0 | 0 |
| 49 | 0 | 0 | — | 0 | 100 | 0 | — | — | 0 | 0 | 0 |
| 177 | 97 | 39 | 98 | 25 | 95 | 99 | — | — | 37 | 0 | 0 |
| 178 | 91 | 0 | — | 25 | 74 | 0 | — | — | 0 | 0 | 0 |
| 47 | 100 | 39 | — | 76 | 97 | 0 | — | — | 0 | 0 | 0 |
| 188 | 92 | 76 | — | 47 | 91 | 0 | — | — | 54 | 0 | 0 |
| 237 | 100 | 0 | — | 0 | 8 | 0 | — | — | 0 | 0 | 0 |
| 123 | 100 | 0 | — | 24 | 0 | 0 | — | — | 0 | 0 | 0 |
| 121 | — | — | — | — | 39 | — | — | — | — | — | — |
| 174 | 0 | 46 | — | 0 | — | 0 | — | — | 0 | 0 | 0 |
| 189 | 80 | 72 | — | 99 | 100 | 0 | — | — | 0 | 0 | 0 |
| 459 | 46 | 0 | — | 0 | 36 | 8 | — | — | 0 | 0 | 0 |
| 46 | 30 | 100 | 99 | 99 | 100 | 0 | 42 | 23 | 0 | 19 | 0 |
| 11 | 0 | 0 | — | 0 | 22 | 0 | — | — | 0 | 0 | 0 |
| 7 | 0 | 57 | — | 0 | 62 | 0 | — | — | 0 | 0 | 0 |
| 133 | 51 | 0 | — | 0 | 45 | 0 | — | — | 0 | 0 | 0 |
| 130 | 51 | 40 | — | 0 | 97 | 0 | — | — | 0 | 0 | 0 |
| 122 | 25 | 0 | — | 0 | 44 | 0 | — | — | 0 | 0 | 0 |
| 44 | 68 | 21 | — | 0 | 98 | 47 | — | — | 0 | 0 | 0 |
| 84 | 85 | 0 | — | 99 | 98 | 5 | — | — | 38 | 0 | 0 |
| 85 | 71 | 82 | — | 0 | 100 | 0 | — | — | 0 | 36 | 27 |
| 106 | 93 | 35 | — | 24 | 100 | 5 | — | — | 38 | 0 | 0 |

-continued

| CMPD NO. | EX. A | EX. B | EX. C | EX. D | EX. E | EX. F | EX. G | EX. H | EX. I | EX. J | EX. K |
|---|---|---|---|---|---|---|---|---|---|---|---|
| 113 | 0 | 0 | — | 46 | 100 | 5 | — | — | 0 | 0 | 0 |
| 62 | 0 | 65 | — | 46 | 100 | 5 | — | — | 0 | 0 | 0 |
| 78 | 51 | 0 | — | 0 | 88 | 5 | — | — | 0 | 0 | 0 |
| 160 | 0 | 82 | — | 46 | 100 | 0 | — | — | 0 | 0 | 85 |
| 192 | 91 | 78 | — | 97 | 97 | 6 | — | — | 0 | 0 | 0 |
| 176 | 61 | 22 | — | 0 | 99 | 0 | — | — | 38 | 0 | 0 |
| 60 | 61 | 100 | — | 99 | 100 | 0 | 69 | 100 | 0 | 62 | 97 |
| 199 | 0 | 79 | 0 | 0 | — | 0 | — | — | 39 | 0 | 25 |
| 179 | 60 | 59 | — | 0 | — | 0 | — | — | 39 | 0 | 25 |
| 43 | 35 | 95 | — | 93 | 100 | 6 | — | — | 0 | 0 | 27 |
| 92 | 0 | 0 | — | 0 | 7 | 0 | — | — | 0 | 0 | 0 |
| 93 | 0 | 24 | — | 26 | 40 | 0 | — | — | 0 | 0 | 0 |
| 103 | 32 | 90 | — | 26 | 99 | 0 | — | — | 0 | 0 | 0 |
| 63 | 32 | 79 | 100 | 99 | 100 | 0 | — | — | 0 | 0 | 0 |
| 61 | 79 | 90 | 100 | 99 | 100 | 42 | — | — | 0 | 0 | 25 |
| 74 | 39 | 12 | — | 26 | 27 | 0 | — | — | 23 | 0 | 0 |
| 238 | 5 | 95 | — | 0 | — | 0 | — | — | 54 | 0 | 0 |
| 330 | 11 | 83 | 100 | 93 | 100 | 45 | 100 | 100 | 0 | 0 | 27 |
| 190 | 11 | 0 | — | 0 | — | 5 | — | — | 0 | 0 | 0 |
| 104 | 43 | 0 | — | 0 | 5 | 0 | — | — | 36 | 0 | 27 |
| 202 | 11 | 0 | — | 26 | 94 | 5 | — | — | 0 | 0 | 0 |
| 247 | 64 | 81 | — | 97 | 100 | 0 | — | — | 0 | 0 | 67 |
| 195 | 17 | 0 | — | 26 | — | 89 | — | — | 38 | 0 | 0 |
| 198 | 15 | 26 | — | 0 | — | 66 | — | — | 0 | 0 | 0 |
| 41 | 92 | 21 | — | 46 | 98 | 0 | — | — | 0 | 0 | 26 |
| 64 | 85 | 65 | — | 92 | 100 | 0 | — | — | 62 | 0 | 0 |
| 213 | 39 | 12 | — | 0 | — | 0 | — | — | 0 | 0 | 0 |
| 203 | 43 | 0 | — | 0 | 5 | 0 | — | — | 0 | 0 | 0 |
| 107 | 15 | 0 | — | 26 | 100 | 66 | — | — | 0 | 0 | 0 |
| 342 | — | — | — | 98 | 100 | — | — | — | — | — | — |
| 105 | 15 | 60 | — | 26 | — | 80 | — | — | 0 | 0 | 0 |
| 51 | 0 | 100 | — | 97 | 100 | 80 | — | — | 38 | 0 | 0 |
| 108 | 3 | 96 | 100 | 76 | 100 | 0 | — | — | 0 | 0 | 86 |
| 305 | 0 | 79 | — | 99 | 100 | 0 | — | — | 0 | 0 | 28 |
| 114 | 87 | 96 | — | 97 | — | 0 | — | — | 0 | 0 | 94 |
| 229 | 3 | 24 | — | 24 | — | 0 | — | — | 0 | 0 | 0 |
| 230 | 42 | 0 | — | 0 | — | 0 | — | — | 0 | 0 | 0 |
| 226 | 51 | 0 | — | 0 | — | — | — | — | 0 | 36 | 67 |
| 239 | 73 | 60 | — | 0 | — | 0 | — | — | 0 | 0 | 0 |
| 242 | 88 | 60 | — | 0 | — | 0 | — | — | 38 | 0 | 0 |
| 243 | 88 | 60 | — | 0 | — | — | — | — | 38 | 0 | 0 |
| 244 | 15 | 60 | — | 0 | — | 41 | — | — | 63 | 0 | 0 |
| 231 | 15 | 0 | — | 77 | 87 | 41 | — | — | 0 | 0 | 27 |
| 232 | 49 | 0 | — | 0 | — | 0 | — | — | 0 | 0 | 0 |
| 136 | 15 | 60 | — | 0 | — | 0 | — | — | 0 | 0 | 0 |
| 241 | 0 | 60 | — | 0 | — | 41 | — | — | 0 | 0 | 0 |
| 228 | 0 | 26 | — | 0 | — | 0 | — | — | 0 | 0 | 0 |
| 141 | 73 | 0 | — | 0 | — | 0 | — | — | 0 | 0 | 0 |
| 140 | 15 | 26 | — | 0 | — | 0 | — | — | 0 | 0 | 0 |
| 240 | 0 | 80 | — | 0 | — | 0 | — | — | 0 | 0 | 0 |
| 185 | 15 | 26 | — | 0 | — | 41 | — | — | 0 | 0 | 27 |
| 227 | 0 | 0 | — | 0 | — | 0 | — | — | 0 | 0 | 0 |
| 245 | 15 | 26 | — | 0 | — | 0 | — | — | 0 | 0 | 0 |
| 222 | 15 | 26 | — | 77 | 100 | 41 | — | — | 38 | 0 | 0 |
| 301 | 90 | 81 | 100 | 99 | 100 | 0 | — | — | 0 | 0 | 0 |
| 291 | 4 | 100 | — | 99 | 100 | 0 | — | — | 0 | 0 | 0 |

What is claimed is:
1. A method of controlling fungus disease in plants that comprises treating the locus to be protected with an effective amount of a compound of Formula I

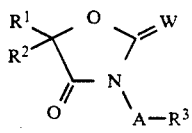

wherein:
A is O or NR$^4$;
W is O or S;
R$^1$ is H; C$_1$ to C$_6$ alkyl; C$_1$ to C$_6$ haloalkyl; C$_3$ to C$_6$ cycloalkyl; C$_2$ to C$_6$ alkenyl; C$_2$ to C$_6$ alkynyl; C$_2$ to C$_6$ alkoxyalkyl; C$_1$ to C$_3$ alkyl substituted with C$_3$ to C$_6$ cycloalkyl, phenyl or benzyl, wherein said phenyl or benzyl ring is substituted on the ring with R$^6$, and the benzylic carbon is substituted with R$^7$;

R$^2$ is phenyl substituted with R$^5$ and R$^6$; naphthyl substituted with 1 to 2 groups selected from R$^6$; thienyl substituted with R$^5$ and R$^6$; furyl substituted with R$^6$;

C$_1$ to C$_2$ alkyl substituted with phenoxy or phenylthio, said phenoxy or phenylthio being substituted on the ring with R$^6$; C$_1$ to C$_6$ alkyl; or C$_5$ to C$_7$ cycloalkyl; and R$^1$ and R$^2$ can be taken together, along with the carbon to which they are attached, to form a carbocyclic or heterocyclic ring having a O, or S of 5 to 7 ring atoms in which the heterocyclic ring can be fused with an R$^5$-substituted benzene ring or an R$^6$-substituted thiophene ring, the heteroatom not being attached to the spiro center; and the carbocyclic ring can be fused with 1 or 2 $R^5$-substituted benzene rings or with an $R^6$-substituted thiophene ring;

$R^3$ is phenyl substituted with $R^{10}$; benzyl substituted on the benzylic carbon with a group selected from $R^7$ and substituted on the phenyl ring with $R^{10}$; naphthyl substituted with $R^{10}$; additionally, $R^3$ can be thienyl substituted with $R^{10}$, furyl substituted with $R^{10}$; or $R^3$ can be $C_2$ to $C_{10}$ alkyl or $C_5$ to $C_7$ cycloalkyl;

$R^4$ is hydrogen; formyl; $C_2$ to $C_4$ alkylcarbonyl; $C_2$ to $C_4$ haloalkylcarbonyl; $C_2$ to $C_4$ alkoxyalkyl-carbonyl; $C_2$ to $C_4$ alkoxycarbonyl; $C_2$ to $C_5$ alkylaminocarbonyl; $C_1$ to $C_4$ alkylsulfonyl; $C_1$ to $C_4$ alkyl; $C_4$ to $C_6$ cycloalkyl; phenylamino-carbonyl where said phenyl is substituted with $R^{10}$; and $R^4$ can be $C_3$ to $C_4$ alkenyl or $C_3$ to $C_4$ alkynyl; or $R^3$ and $R^4$ can be taken together, along with the nitrogen atom to which they are attached, to form a pyrrolidino, or pyrrolo ring substituted with $R^{10}$, which rings can be fused to an $R^{10}$-substituted benzene ring;

$R^5$ is hydrogen; halogen; $C_1$ to $C_{12}$ alkyl; $C_1$ to $C_{12}$ haloalkyl; $C_1$ to $C_{12}$ alkoxy; $C_3$ to $C_{12}$ alkenyl; $C_3$ to $C_{12}$ haloalkenyl; $C_3$ to $C_{12}$ alkenyloxy; $C_3$ to $C_{12}$ alkynyl; $C_3$ to $C_{12}$ haloalkynyl; $C_3$ to $C_{12}$ alkylthio; $C_1$ to $C_{12}$ haloalkylthio; $C_1$ to $C_{12}$ haloalkoxy; $C_1$ to $C_{12}$ alkylsulfonyl; $C_1$ to $C_{12}$ haloalkylsulfonyl; nitro; phenyl substituted with $R^6$; phenoxy substituted with $R^6$; phenylthio substituted with $R^6$; cyano; $C_3$ to $C_{12}$ alkynyloxy; $C_2$ to $C_{12}$ alkoxyalkyl; $C_2$ to $C_{12}$ alkoxyalkoxy; phenoxymethyl substituted on the phenyl ring with $R^6$; benxyloxy substituted on the phenyl ring with $R^6$; phenethoxy substituted on the phenyl ring with $R^6$; phenethyl substituted on the phenyl ring with $R^6$; benzyl substituted on the phenyl ring with $R^6$; $C_2$ to $C_{12}$ carboalkoxy; $C_5$ to $C_6$ cycloalkyl; $NMe_2$; or $NR^8R^9$;

$R^6$ is hydrogen; 1 to 2 halogen; $C_1$ to $C_4$ alkyl; trifluoromethyl; $C_1$ to $C_4$ alkoxy; methylthio; nitro; phenoxy; $C_2$ to $C_6$ cycloalkyloxy; or $C_5$ to $C_6$ cycloalkyl;

$R^7$ is hydrogen; or $C_1$ to $C_4$ alkyl;

$R^8$ is H; or $C_1$ to $C_4$ alkyl;

$R^9$ is H; phenyl substituted with H; 1–2 halogen; $CF_3$; $C_1$ to $C_2$ alkyl or $C_5$ to $C_2$ alkoxy; and $R^{10}$ is 0–2 groups selected from $CF_3$; $CF_3O$; $NO_2$; $CO_2Me$; halogen; $C_1$ to $C_5$ alkyl; $C_1$ to $C_5$ alkoxy; or $CN$; provided that when the $R^3$ ring is disubstituted, one of the $R^{10}$ alkyl or alkoxy groups is no larger than methyl or methoxy;

provided that, (1) when A is oxygen, $R^3$ is phenyl substituted with $R^{10}$, and (2) when A is $NR^4$;

$R^2$ is phenyl substituted with $R^5$ and $R^6$; naphthyl substituted with 1 to 2 groups selected from $R^6$; $C_1$ to $C_2$ alkyl substituted with phenoxy or phenylthio, said phenoxy or phenylthio being substituted on the ring with $R^6$; or $C_1$ to $C_6$ alkyl;

$R^5$ is hydrogen; halogen; $C_1$ to $C_6$ alkyl; $C_1$ to $C_6$ haloalkyl; $C_1$ to $C_6$ alkoxy; $C_3$ to $C_{12}$ alkenyloxy; $C_1$ to $C_5$ alkylthio; $C_1$ to $C_4$ haloalkylthio; $C_1$ to $C_4$ haloalkoxy; $C_1$ to $C_4$ alkylsulfonyl; $C_1$ to $C_4$ haloalkylsulfonyl; nitro, phenyl substituted with $R^6$; phenoxy substituted with $R^6$; phenylthio substituted with $R^6$; cyano; $C_3$ to $C_4$ alkynyloxy; $C_2$ to $C_6$ alkoxyalkyl; $C_2$ to $C_6$ alkoxyalkoxy; phenoxymethyl substituted on the phenyl ring with $R^6$; benzyloxy substituted on the phenyl ring with $R^6$; phenethyloxy substituted on the phenyl ring with $R^6$; phenethyl substituted on the phenyl ring with $R^6$; benzyl substituted on the phenyl ring with $R^6$; $C_2$ to $C_6$ carboalkoxy; or $C_5$ to $C_6$ cycloalkyl; and $R^6$ is hydrogen; 1 to 2 halogen; methyl; trifluoromethyl; $C_1$ to $C_4$ alkoxy; methylthio; or nitro;

then $R^3$ is other than phenyl substituted with $R^{10}$, benzyl substituted on the benzylic carbon with a group selected from $R^7$ and substituted on the phenyl ring with $R^{10}$; or naphthyl substituted with $R^{10}$.

2. The method of claim 1 wherein

A is $NR^4$;

$R^1$ is $C_1$ to $C_4$ alkyl; $C_1$ to $C_3$ haloalkyl vinyl; ethynyl; or methoxymethyl;

$R^2$ is $C_5$ to $C_7$ cycloalkyl; or thienyl substituted with $R^6$;

$R^3$ is phenyl substituted with $R^{10}$; and $R^4$ is H; $C_1$ to $C_3$ alkyl; or $C_1$ to $C_3$ alkylcarbonyl.

3. A compound of the Formula IA

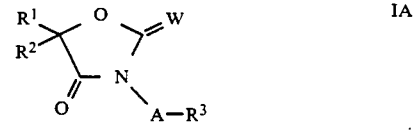

IA wherein:

A is O or $NR^4$;

W is O or S;

$R^1$ is H; $C_1$ to $C_6$ alkyl; $C_1$ to $C_6$ haloalkyl; $C_3$ to $C_6$ cycloalkyl; $C_2$ to $C_6$ alkenyl; $C_2$ to $C_6$ alkynyl; $C_2$ to $C_6$ alkoxyalkyl; $C_1$ to $C_3$ alkyl substituted with $C_3$ to $C_6$ cycloalkyl, phenyl or benzyl, wherein said phenyl or benzyl ring is substituted on the ring with $R^6$, and the benzylic carbon is substituted with $R^7$;

$R^2$ is phenyl substituted with $R^5$ and $R^6$; naphthyl substituted with 1 to 2 groups selected from $R^6$; thienyl substituted with $R^5$ and $R^6$; furyl substituted with $R^6$;

$C_1$ to $C_2$ alkyl substituted with phenoxy or phenylthio, said phenoxy or phenylthio being substituted on the ring with $R^6$; $C_1$ to $C_6$ alkyl; or $C_5$ to $C_7$ cycloalkyl; and $R^1$ and $R^2$ can be taken together, along with the carbon to which they are attached, to form a carbocyclic or heterocyclic ring (having a O, or S of 5 to 7 or having N—$R^7$ of 5 ring atoms in which the heterocyclic ring can be fused with an $R^5$-substituted benzene ring or an $R^6$-substituted thiophene ring, the heteroatom not being attached to the spiro center; and the carbocyclic ring can be fused with 1 or 2 $R^5$-substituted benzene rings or with an $R^6$-substituted thiophene ring;

$R^3$ is phenyl substituted with $R^{10}$; benzyl substituted on the benzylic carbon with a group selected from $R^7$ and substituted on the phenyl ring with $R^{10}$; naphthyl substituted with $R^{10}$; additionally, $R^3$ can be thienyl substituted with $R^{10}$, furyl substituted with $R^{10}$; or $R^3$ can be $C_2$ to $C_{10}$ alkyl or $C_5$ to $C_7$ cycloalkyl;

$R^4$ is hydrogen; formyl; $C_2$ to $C_4$ alkylcarbonyl; $C_2$ to $C_4$ haloalkylcarbonyl; $C_2$ to $C_4$ alkoxyalkyl-carbonyl; $C_2$ to $C_4$ alkoxycarbonyl; $C_2$ to $C_5$ alkylaminocarbonyl; $C_1$ to $C_4$ alkylsulfonyl; $C_1$ to $C_4$ alkyl; $C_4$ to $C_6$ cycloalkyl; phenylamino-carbonyl where said phenyl is substituted with $R^{10}$; and $R^4$ can be $C_3$ to $C_4$ alkenyl or $C_3$ to $C_4$ alkynyl; or $R^3$ and $R^4$ can be taken together, along with the nitrogen atom to which they are attached, to form a pyrrolidino, or pyrrolo ring substituted with $R^{10}$, which rings can be fused to an $R^{10}$-substituted benzene ring;

$R^5$ is hydrogen; halogen; $C_1$ to $C_{12}$ alkyl; $C_1$ to $C_{12}$ haloalkyl; $C_1$ to $C_{12}$ alkoxy; $C_3$ to $C_{12}$ alkenyl; $C_3$ to $C_{12}$ haloalkenyl; $C_3$ to $C_{12}$ alkenyloxy; $C_3$ to $C_{12}$ alkynyl; $C_3$ to $C_{12}$ haloalkenyl; $C_3$ to $C_{12}$ alkylthio; $C_1$ to $C_{12}$ haloalkylthio; $C_1$ to $C_{12}$ haloalkoxy; $C_1$ to $C_{12}$ alkylsulfonyl; $C_1$ to $C_{12}$ haloalkylsulfonyl; nitro; phenyl substituted with $R^6$; phenoxy substituted with $R^6$; phenylthio substituted with $R^6$; cyano; $C_3$ to $C_{12}$ alkynyloxy; $C_2$ to $C_{12}$ alkoxyalkyl; $C_2$ to $C_{12}$ alkoxyalkoxy; phenoxymethyl substituted on the phenyl ring with $R^6$; benzyloxy substituted on the phenyl ring with $R^6$; phenethyl substituted on the phenyl ring with $R^6$; benzyl substituted on the phenyl ring with $R^6$; $C_2$ to $C_{12}$ carboalkoxy; $C_5$ to $C_6$ cycloalkyl; $NMe_2$; or $NR^8R^9$;

$R^6$ is hydrogen; 1 to 2 halogen; $C_1$ to $C_4$ alkyl; trifluoromethyl; $C_1$ to $C_4$ alkoxy; methylthio, nitro; phenoxy; $C_2$ to $C_6$ cycloalkyloxy; or $C_5$ to $C_6$ cycloalkyl;

$R^7$ is hydrogen; or $C_1$ to $C_4$ alkyl;

$R^8$ is H; or $C_1$ to $C_4$ alkyl;

$R^9$ is H; phenyl substituted with H; 1-2 halogen; $CF_3$; $C_1$ to $C_2$ alkyl; or $C_1$ to $C_2$ alkoxy; and $R^{10}$ is 0-2 groups selected from $CF_3$; $CF_3O$; $NO_2$; $CO_2Me$; halogen; $C_1$ to $C_5$ alkyl; $C_1$ to $C_5$ alkoxy; or CN; provided that when the $R^3$ ring is disubstituted, one of the $R^{10}$ alkyl or alkoxy groups is no larger than methyl or methoxy; provided that (1) when A is O, then $R^3$ is phenyl substituted with $R^{10}$;

(2) when $R^2$ is phenyl and $R^5$ and $R^6$ are hydrogen, then $R^1$ is not hydrogen, methyl or benzyl;

(3) when $R^1$ is hydrogen, methyl or cyclohexyl, then $R^2$ is not methyl, isopropyl or cyclohexyl; and (4) $R^1$ and $R^2$ do not join to form $—(CH_2)_5—$.

4. A compound of claim 3 wherein

A is $NR^4$;

$R^1$ is $C_1$ to $C_4$ alkyl; $C_1$ to $C_3$ haloalkyl; vinyl; ethynyl; or methoxymethyl;

$R^2$ is phenyl substituted with $R^5$ and $R^6$; $C_5$ to $C_7$ cycloalkyl; or thienyl substituted with $R^6$;

$R^3$ is phenyl substituted with $R^{10}$; and $R^4$ is H; $C_1$ to $C_3$ alkyl; or $C_1$ to $C_3$ alkylcarbonyl.

5. A compound of claim 4 wherein $R^1$ is $C_1$ to $C_4$ alkyl or vinyl;

$R^2$ is phenyl substituted with $R^5$ and $R^6$;

$R^3$ is phenyl substituted with 1-2 halogen, methyl or methoxy;

$R^4$ is hydrogen or methyl;

$R^5$ is hydrogen; halogen; $C_1$ to $C_4$ alkyl; $C_1$ to $C_4$ haloalkyl; $C_1$ to $C_6$ alkoxy; benzyloxy; $F_3CO$; $F_2HCO$; $C_1$ to $C_6$ haloalkoxy; phenoxy substituted with $R^6$; provided that if $R^5$ is not H or F, then it is para to the point of attachment to the ring;

$R^6$ is hydrogen, 1 to 2 F or Cl; methyl; or methoxy; and $R^7$ is hydrogen.

6. A compound of claim 5 wherein $R^1$ is $CH_3$;

$R^4$ is hydrogen or methyl;

$R^5$ is H; F; Cl; $CH_3$; $C_1$ to $C_6$ alkoxy; or phenoxy substituted with halogen, $CH_3$, $CH_3O$ or $NO_2$;

$R^6$ is H or F; and $R^{10}$ is F; H or $CH_3$.

7. A compound of claim 3 selected from the class consisting of:

5-methyl-5-(4-phenoxyphenyl)-3-(phenylamino)-2-thioxo-4-oxazolidinone; and the (S)-enantiomer thereof;

5-methyl-5-phenyl-3-(-N'-phenyl-N'-methylamino)-2-thiozo-4-oxazolidinone; and the (S)-enantiomer thereof;

5-(4-(4-bromophenoxy)phenyl)-5-methyl-3-(phenylamino)-2-thioxo-4-oxazolidinone; and the (S)-enantiomer thereof;

5-[4-(3-fluorophenoxy)phenyl]-5-methyl-3(phenylamino)-2-thioxo-4-oxazolidinone; and the (S)-enantiomer thereof;

5-(2,4-difluorophenyl)-5-methyl-3-(phenylamino)-2,4-oxazolidinedione; and the (S)-enantiomer thereof;

5-methyl-5-(4-phenoxyphenyl)-3-(phenylamino)-2,4-oxazolidinedione; and the (S)-enantiomer thereof; and mixtures of the foregoing.

8. An agriculturally suitable composition comprising a fungicidally effective amount of a compound of claim 3 and at least one of the following: surfactant, solid diluent or liquid diluent.

9. An agriculturally suitable composition comprising a fungicidally effective amount of a compound of claim 4 and at least one of the following: surfactant, solid diluent or liquid diluent.

10. An agriculturally suitable composition comprising a fungicidally effective amount of a compound of claim 5 and at least one of the following; surfactant, solid diluent or liquid diluent.

11. An agriculturally suitable composition comprising a fungicidally effective amount of a compound of claim 6 and at least one of the following: surfactant, solid diluent or liquid diluent.

12. An agriculturally suitable composition comprising a fungicidally effective amount of a compound of claim 7 and at least one of the following: surfactant, solid diluent or liquid diluent.

13. A method of controlling fungus disease in plants that comprises treating the locus to be protected with an effective amount of a combination of a compound of Formula I of claim 1 with cymoxanil.

14. An agriculturally suitable composition comprising a fungicidally effective amount of a combination of a compound of claim 3 and cymoxanil and at least one of the following: surfactant, solid diluent or liquid diluent.

* * * * *